(12) United States Patent
Wang et al.

(10) Patent No.: US 8,192,952 B2
(45) Date of Patent: *Jun. 5, 2012

(54) GENETICALLY ENCODED FLUORESCENT COUMARIN AMINO ACIDS

(75) Inventors: Jiangyun Wang, San Diego, CA (US); Jianming Xie, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 310 days.

This patent is subject to a terminal disclaimer.

(21) Appl. No.: 12/227,383

(22) PCT Filed: May 21, 2007

(86) PCT No.: PCT/US2007/012361
§ 371 (c)(1),
(2), (4) Date: Apr. 9, 2009

(87) PCT Pub. No.: WO2007/139870
PCT Pub. Date: Dec. 6, 2007

(65) Prior Publication Data
US 2009/0298119 A1 Dec. 3, 2009

Related U.S. Application Data

(60) Provisional application No. 60/813,856, filed on Jun. 14, 2006, provisional application No. 60/808,099, filed on May 23, 2006.

(51) Int. Cl.
*C12P 21/00* (2006.01)
*C12N 15/74* (2006.01)
*C12N 1/21* (2006.01)
(52) U.S. Cl. ....... 435/69.1; 435/325; 435/183; 536/23.2
(58) Field of Classification Search .................. None
See application file for complete search history.

(56) References Cited

U.S. PATENT DOCUMENTS

| | | | |
|---|---|---|---|
| 5,998,593 | A | 12/1999 | Huff et al. |
| 6,927,042 | B2 | 8/2005 | Schultz et al. |
| 7,045,337 | B2 | 5/2006 | Schultz et al. |
| 7,083,970 | B2 | 8/2006 | Schultz et al. |
| 7,129,333 | B2 | 10/2006 | Schultz et al. |
| 7,183,082 | B2 | 2/2007 | Schultz et al. |
| 7,199,222 | B2 | 4/2007 | Schultz et al. |
| 7,217,809 | B2 | 5/2007 | Schultz et al. |
| 7,238,510 | B2 | 7/2007 | Schultz et al. |
| 7,262,040 | B2 | 8/2007 | Schultz et al. |
| 2003/0108885 | A1 | 6/2003 | Schultz et al. |
| 2004/0198637 | A1 | 10/2004 | Schultz et al. |
| 2004/0265952 | A1 | 12/2004 | Deiters et al. |
| 2005/0009049 | A1 | 1/2005 | Chin et al. |
| 2005/0136513 | A1 | 6/2005 | Zhang et al. |
| 2005/0208536 | A1 | 9/2005 | Schultz et al. |
| 2005/0227318 | A1 | 10/2005 | Alfonta et al. |
| 2005/0272121 | A1 | 12/2005 | Xie et al. |
| 2006/0063244 | A1 | 3/2006 | Schultz et al. |
| 2006/0068478 | A1 | 3/2006 | Schultz et al. |
| 2006/0073507 | A1 | 4/2006 | Deiters et al. |
| 2006/0110784 | A1 | 5/2006 | Deiters et al. |
| 2006/0110796 | A1 | 5/2006 | Schultz et al. |
| 2006/0134746 | A1 | 6/2006 | Deiters et al. |
| 2006/0160175 | A1 | 7/2006 | Anderson et al. |
| 2006/0177900 | A1 | 8/2006 | Anderson et al. |
| 2006/0234367 | A1 | 10/2006 | Schultz et al. |
| 2006/0246509 | A1 | 11/2006 | Deiters et al. |
| 2007/0009990 | A1 | 1/2007 | Alfonta et al. |
| 2007/0020634 | A1 | 1/2007 | Anderson et al. |
| 2007/0042461 | A1 | 2/2007 | Anderson et al. |
| 2007/0111193 | A1 | 5/2007 | Zhang et al. |
| 2007/0154952 | A1 | 7/2007 | Chin et al. |
| 2007/0166791 | A1 | 7/2007 | Chin et al. |
| 2007/0172915 | A1 | 7/2007 | Schultz et al. |
| 2007/0178448 | A1 | 8/2007 | Tsao et al. |
| 2007/0184517 | A1 | 8/2007 | Schultz et al. |
| 2007/0238152 | A1 | 10/2007 | Wang et al. |

FOREIGN PATENT DOCUMENTS

| | | |
|---|---|---|
| WO | WO 02/085923 A2 | 10/2002 |
| WO | WO 2006/110182 | 12/2006 |
| WO | WO 2007/103490 | 9/2007 |

OTHER PUBLICATIONS

Brun et al. (2004) "A Very Short Route to Enantiomerically Pure Coumarin-Bearing Fluorescent Amino Acids." *Angew. Chem., Int. Ed.*, (2004) 43(26): 3432-3436.
Feng et al. (2003) "Expanding tRNA recognition of a tRNA synthetase by a single amino acid change" *Proceedings of the National Academy of Sciences, USA*, 100(10): 5676-5681.
Forster et al.,(2003) "Programming peptidomimetic synthetases by translating genetic codes designed de novo." *Proceedings of the National Academy of Sciences, USA*, 100(11): 6353-6357.
Hohsaka et al. (2004) "Position-specific incorporation of dansylated non-natural amino acids into streptavidin by using a four-base codon." *FEBS Letters*, 560: 173-177. Mendel et al. (1995) "Site-directed Mutagenesis with an Expanded Genetic Code." *Annual Review of Biophysics & Biomolecular Structure*, 24: 435-462.
Wang and Schultz (2005) "Expanding the Genetic Code," *Angewandte Chemie Int. Ed.*, 44(1): 34-66.
Wang and Schultz (2002) "Expanding the Genetic Code," *Chem. Commun.*, 1: 1-11.
Wang et al. (2006) "Expanding the Genetic Code," *Annual Review of Biophysics & Biomolecular Structure*, 35: 225-249.
Xie and Schultz (2006) "A chemical toolkit for proteins—an expanded genetic code," *Nature Reviews: Molecular Cell Biology*, 7(10): 775-782.
Xie and Schultz (2005) "Adding Amino Acids to the Genetic Repertoire." *Current Opinion in Chemical Biology*, 9(6): 548-554.

(Continued)

*Primary Examiner* — Kagnew H Gebreyesus
(74) *Attorney, Agent, or Firm* — Quine Intellectual Property Law Group, P.C.

(57) ABSTRACT

The invention relates to orthogonal pairs of tRNAs and aminoacyl-tRNA synthetases that can incorporate the coumarin unnatural amino acid L-(7-hydroxycoumarin-4-yl)ethylglycine into proteins produced in eubacterial host cells such as *E. coli*. The invention provides, for example but not limited to, novel orthogonal synthetases, methods for identifying and making the novel synthetases, methods for producing proteins containing the unnatural amino acid L-(7-hydroxycoumarin-4-yl)ethylglycine and related translation systems.

38 Claims, 6 Drawing Sheets

OTHER PUBLICATIONS

Xie and Schultz (2005) "An Expanding Genetic Code," *Methods*, 36(3): 227-238.

Wang et al. (2006) "A Genetically Encoded Fluorescent Amino Acid." *Journal of the American Chemistry Society*, 128: 8738-8739.

Wang and Schultz (2001) "A general approach for the generation of orthogonal tRNAs." *Chemistry & Biology*, 8: 883-890.

Chin et al. (2003) "An Expanded Eukaryotic Genetic Code." *Science*, 301: 964-967.

Wang et al. (2001) "Expanding the Genetic Code of *Escherichia coli.*" *Science*, 292: 498-500.

Wang et al. (2003) "Addition of the keto functional group to the genetic code of *Escherichia coli.*" *Proceedings of the National Academy of Sciences, USA*, 100(1): 56-61.

Pastrnak et al. (2000) "A New Orthogonal Suppressor tRNA/Aminoacyl-tRNA Synthatase Pair for Evolving an Organism with an Expanded Genetic Code." *Helvetica Chemica Acta*, 83: 2277-2285.

Furter (1998) "Expansion of the genetic code: Site-directed p-fluoro-phenylalanine infororation in *Escherichia.*" *Protein Science*, 7: 419-426.

(1) L-(7-hydroxycoumarin-4-yl) ethylglycine
(2) N-α-Cbz-L-glutamic acid α-benzyl ester
(3) (2S)-2 benzyloxycarbonylamino-5-oxo-heptanedioic acid 1-benzyl ester 7-ethyl ester Nucleotide and Amino Acid Sequences

| SEQ ID NO: | Description | SEQUENCE |
|---|---|---|
| 1 | *Methanococcus jannaschii* - suppressor tyrosyl-tRNA$_{CUA}$ aka MjtRNA-Tyr(CUA) or mutRNA$_{CUA}^{Tyr}$ | CCGGCGGUAGUUCAGCAGGGCAGAACGGCGGACUCUAAAUCCG CAUGGCGCUGGUUCAAAUCCGGCCCGCCGGACCA |
| 2 | Wild-type *Methanococcus jannaschii* tyrosyl-tRNA synthetase (MjTyrRS) amino acid sequence | MDEFEMIKRNTSEIISEEELREVLKKDEKSAYIGFEPSGKIHL GHYLQIKKMIDLQNAGFDIIILLADLHAYLNQKGELDEIRKIG DYNKKVFEAMGLKAKYVYGSEFQLDKDYTLNVYRLALKTTLKR ARRSMELIAREDENPKVAEVIYPIMQVNDIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 3 | Wild-type *Methanococcus jannaschii* tyrosyl-tRNA synthetase (MjTyrRS) nucleotide sequence | ATGGACGAATTTGAAATGATAAAGAGAAACACATCTGAAATTATCAGC GAGGAAGAGTTAAGAGAGGTTTTAAAAAAAGATGAAAAATCTGCTTAC ATAGGTTTTGAACCAAGTGGTAAAATACATTTAGGGCATTATCTCCAA ATAAAAAAGATGATTGATTTACAAAATGCTGGATTTGATATAATTATA TTGTTGGCTGATTTACACGCCTATTTAAACCAGAAAGGAGAGTTGGAT GAGATTAGAAAAATAGGAGATTATAACAAAAAAGTTTTTGAAGCAATG GGGTTAAAGGCAAAATATGTTTATGGAAGTGAATTCCAGCTTGATAAG GATTATACACTGAATGTCTATAGATTGGCTTTAAAAACTACCTTAAAA AGAGCAAGAAGGAGTATGGAACTTATAGCAAGAGAGGATGAAAATCCA AAGGTTGCTGAAGTTATCTATCCAATAATGCAGGTTAATGATATTCAT TATTTAGGCGTTGATGTTGCAGTTGGAGGGGATGGAGCAGAGAAAATA CACATGTTAGCAAGGGAGCTTTTACCAAAAAAGGTTGTTTGTATTCAC AACCCTGTCTTAACGGGTTTGGATGGAGAAGGAAAGATGAGTTCTTCA AAAGGGAATTTTATAGCTGTTGATGACTCTCCAGAAGAGATTAGGGCT AAGATAAAGAAAGCATACTGCCCAGCTGGAGTTGTTGAAGGAAATCCA ATAATGGAGATAGCTAAATACTTCCTTGAATATCCTTTAACCATAAAA AGGCCAGAAAAATTTGGTGGAGATTTGACAGTTAATAGCTATGAGGAG TTAGAGAGTTTATTTAAAAATAAGGAATTGCATCCAATGGATTTAAAA AATGCTGTAGCTGAAGAACTTATAAAGATTTTAGAGCCAATTAGAAAG AGATTA |
| 4 | L-(7-hydroxycoumarin-4-yl) ethylglycine aminoacyl-tRNA synthetase amino acid sequence (derived from wild-type *Methanococcus jannaschii* tyrosyl tRNA-synthetase) | MDEFEMIKRNTSEIISEEELREVLKKDEKSAEIGFEPSGKIHL GHYLQIKKMIDLQNAGFDIIIHLGDLGAYLNQKGELDEIRKI GDYNKKVFEAMGLKAKYVYGSEVHLDKDYTLNVYRLALKTTL KRARRSMELIAREDENPKVAEVIYPIMQVNGIHYGGVDVAVG GMEQRKIHMLARELLPKKVVCIHNPVLTGLDGEGKMSSSKGNF IAVDDSPEEIRAKIKKAYCPAGVVEGNPIMEIAKYFLEYPLTI KRPEKFGGDLTVNSYEELESLFKNKELHPMDLKNAVAEELIKI LEPIRKRL |

Fig. 9

| SEQ ID NO: | Description | SEQUENCE |
|---|---|---|
| 5 | L-(7-hydroxycoumarin-4-yl) ethylglycine aminoacyl-tRNA synthetase nucleotide sequence | ATGGACGAATTTGAAATGATAAAGAGAAACACATCTGAAATTATCAGC GAGGAAGAGTTAAGAGAGGTTTTAAAAAAAGATGAAAAATCTGCTGAG ATAGGTTTTGAACCAAGTGGTAAAATACATTTAGGGCATTATCTCCAA ATAAAAAAGATGATTGATTTACAAAATGCTGGATTTGATATAATTATA CATTTGGGTGATTTAGGCGCCTATTTAAACCAGAAAGGAGAGTTGGAT GAGATTAGAAAAATAGGAGATTATAACAAAAAAGTTTTTGAAGCAATG GGGTTAAAGGCAAAATATGTTTATGGAAGTGAATATCATCTTGATAAG GATTATACACTGAATGTCTATAGATTGGCTTTAAAAACTACCTTAAAA AGAGCAAGAAGGAGTATGGAACTTATAGCAAGAGAGGATGAAAATCCA AAGGTTGCTGAAGTTATCTATCCAATAATGCAGGTTAATGGGATTCAT TATGGTGGCGTTGATGTTGCAGTTGGAGGGATGGAGCAGAGAAAAATA CACATGTTAGCAAGGGAGCTTTTACCAAAAAAGGTTGTTTGTATTCAC AACCCTGTCTTAACGGGTTTGGATGGAGAAGGAAAGATGAGTTCTTCA AAAGGGAATTTTATAGCTGTTGATGACTCTCCAGAAGAGATTAGGGCT AAGATAAAGAAAGCATACTGCCCAGCTGGAGTTGTTGAAGGAAATCCA ATAATGGAGATAGCTAAATACTTCCTTGAATATCCTTTAACCATAAAA AGGCCAGAAAAATTTGGTGGAGATTTGACAGTTAATAGCTATGAGGAG TTAGAGAGTTTATTTAAAAATAAGGAATTGCATCCAATGGATTTAAAA AATGCTGTAGCTGAAGAACTTATAAAGATTTTAGAGCCAATTAGAAAG AGATTATAA |

Fig. 9 (continued)

SEQUENCE LISTING

<160> NUMBER OF SEQ ID NOS: 5

<210> SEQ ID NO 1
<211> LENGTH: 77
<212> TYPE: RNA
<213> ORGANISM: Artificial
<220> FEATURE:
<223> OTHER INFORMATION: mutant suppressor tyrosyl-tRNA CUA

<400> SEQUENCE: 1
ccggcgguag uucagcaggg cagaacggcg gacucuaaau ccgcauggcg cugguucaaa      60
uccggcccgc cggacca                                                    77

<210> SEQ ID NO 2
<211> LENGTH: 306
<212> TYPE: PRT
<213> ORGANISM: Methanococcus jannaschii

<400> SEQUENCE: 2

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

```
Leu Leu Ala Asp Leu His Ala Tyr Leu Asn Gln Lys Gly Glu Leu Asp
 65                  70                  75                  80
Glu Ile Arg Lys Ile Gly Asp Tyr Asn Lys Lys Val Phe Glu Ala Met
                 85                  90                  95
Gly Leu Lys Ala Lys Tyr Val Tyr Gly Ser Glu Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Asp Ile His
145                 150                 155                 160
Tyr Leu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
        275                 280                 285
Asn Ala Val Ala Glu Glu Leu Ile Lys Ile Leu Glu Pro Ile Arg Lys
    290                 295                 300
Arg Leu
305

<210> SEQ ID NO 3
<211> LENGTH: 918
<212> TYPE: DNA
<213> ORGANISM: Methanococcus jannaschii

<400> SEQUENCE: 3
atggacgaat ttgaaatgat aaagagaaac acatctgaaa ttatcagcga ggaagagtta      60
agagaggttt taaaaaaaga tgaaaaatct gcttacatag gttttgaacc aagtggtaaa     120
atacatttag gcattatctc caaataaaa aagatgattg atttacaaaa tgctggattt     180
gatataatta tattgttggc tgatttacac gcctatttaa accagaaagg agagttggat     240
gagattagaa aaataggaga ttataacaaa aagttttg aagcaatggg gttaaaggca     300
aaatatgttt atggaagtga attccagctt gataaggatt atacactgaa tgtctataga     360
ttggctttaa aaactacctt aaaaagagca agaaggagta tggaacttat agcaagagag     420
gatgaaaatc caaaggttgc tgaagttatc tatccaataa tgcaggttaa tgatattcat     480
tatttaggcg ttgatgttgc agttggaggg atggagcaga gaaaaataca catgttagca     540
agggagcttt taccaaaaaa ggttgtttgt attcacaacc ctgtcttaac gggtttggat     600
ggagaaggaa agatgagttc ttcaaaaggg aattttatag ctgttgatga ctctccagaa     660
gagattaggg ctaagataaa gaaagcatac tgcccagctg gagttgttga aggaaatcca     720
```

-continued

```
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagatta                                                    918
```

<210> SEQ ID NO 4
<211> LENGTH: 306
<212> TYPE: PRT
<213> ORGANISM: Artificial
<220> FEATURE:
<223> OTHER INFORMATION: L-(7-hydroxycoumarin-4-yl) ethylglycine aminoacyl-tRNA synthetase

<400> SEQUENCE: 4

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Glu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

His Leu Gly Asp Leu Gly Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Tyr His Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Gly Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

-continued

```
<210> SEQ ID NO 5
<211> LENGTH: 921
<212> TYPE: DNA
<213> ORGANISM: Artificial
<220> FEATURE:
<223> OTHER INFORMATION: L-(7-hydroxycoumarin-4-yl) ethylglycine
      aminoacyl-tRNA synthetase

<400> SEQUENCE: 5
atggacgaat ttgaaatgat aaagagaaac acatctgaaa ttatcagcga ggaagagtta        60
agagaggttt taaaaaaaga tgaaaaatct gctgagatag gttttgaacc aagtggtaaa       120
atacatttag ggcattatct ccaaataaaa aagatgattg atttacaaaa tgctggattt       180
gatataatta tacatttggg tgatttaggc gcctatttaa accagaaagg agagttggat       240
gagattagaa aaataggaga ttataacaaa aaagttttg aagcaatggg gttaaaggca        300
aaatatgttt atggaagtga atatcatctt gataaggatt atacactgaa tgtctataga       360
ttggctttaa aaactacctt aaaaagagca agaaggagta tggaacttat agcaagagag       420
gatgaaaatc caaaggttgc tgaagttatc tatccaataa tgcaggttaa tgggattcat       480
tatggtggcg ttgatgttgc agttggaggg atggagcaga gaaaaataca catgttagca       540
agggagcttt taccaaaaaa ggttgtttgt attcacaacc ctgtcttaac gggtttggat       600
ggagaaggaa agatgagttc ttcaaaaggg aatttatag ctgttgatga ctctccagaa        660
gagattaggg ctaagataaa gaaagcatac tgcccagctg gagttgttga aggaaatcca       720
ataatggaga tagctaaata cttccttgaa tatcctttaa ccataaaaag gccagaaaaa       780
tttggtggag atttgacagt taatagctat gaggagttag agagtttatt taaaaataag       840
gaattgcatc caatggattt aaaaaatgct gtagctgaag aacttataaa gattttagag       900
ccaattagaa agagattata a                                                 921
```

GENETICALLY ENCODED FLUORESCENT COUMARIN AMINO ACIDS

CROSS-REFERENCE TO RELATED APPLICATIONS

This application is a 371 of U.S. application Ser. No. 11/805,247, entitled, "Genetically Encoded Fluorescent Coumarin Amino Acids," by Wang, et al., filed Feb. 21, 2008, and claims priority to and benefit of: U.S. Provisional Appl. Ser. No. 60/808,099, entitled "Genetically Encoded Fluorescent Coumarin Amino Acid," by Wang, et al., filed May 23, 2006; and U.S. Provisional Appl. Ser. No. 60/813,856, entitled "A Genetically Encoded Fluorescent Coumarin Amino Acid," by Wang, et al., filed Jun. 14, 2006, the disclosures of which are all hereby incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support from the Department of Energy under Grant No. ER46051. The government has certain rights to this invention.

FIELD OF THE INVENTION

The invention is in the field of translation biochemistry. The invention relates to compositions and methods for making and using orthogonal tRNAs, orthogonal aminoacyl-tRNA synthetases, and pairs thereof, that incorporate unnatural amino acids into proteins. The invention also relates to methods of producing proteins in cells using such pairs and proteins made by the methods.

BACKGROUND OF THE INVENTION

Fluorescence has become one of the most important detection signals in biotechnology due to its high sensitivity and safety of handling. Processes like fluorescence resonance energy transfer (FRET) or fluorescence polarization make possible the real time analysis of biomolecular binding events, movements or conformational changes. The ability to selectively modify proteins with fluorescent probes has greatly facilitated both in vitro and in vivo studies of protein structure and function (Hermanson (1996) in *Bioconjugate Techniques*, Academic Press: San Diego; and Tsien (1998) *Annu. Rev. Biochem.*, 67:509-544).

Current fluorescent methodology to study proteins in vivo often relies on fusion constructs with large fluorescent proteins such as green fluorescent protein (GFP). Although this probe has proven useful in studies of protein expression, localization and bimolecular interactions, its large size can result in significant structural perturbations. GFP fusions are also limited to the C- or N-terminus of the target protein and are relatively insensitive to their environment Crsien (1998) *Annu, Rev. Biochem.*, 67:509-44). GFP also requires many transcripts to achieve a suitable signal, and requires a lag-time for its folding and fluorophore maturation.

Chemical methods also can be used to selectively modify proteins with a variety of small, synthetic fluorophores that minimize structural perturbation (Hermanson, in *Bioconjugate Techniques*, Academic Press: San Diego (1996); Martin et al., *Nat. Biotech.*, 23:1308-1314 (2005); Keppler et al., *Nat. Biotech.*, 21:86-89 (2003); Lin et al., *J. Am. Chem. Sci.*, 128:4542-3 (2006)). However, these techniques are generally limited to uniquely reactive surface accessible residues on isolated proteins (e.g., the modification of cysteine with maleimide derivatives; see Hermanson in *Bioconjugate Techniques* (1996) Academic Press: San Diego), exhibit poor regioselectivity, are cytotoxic or demand introduction of dye binding protein motifs.

Biosynthetic labeling methods using chemically misacylated tRNAs (Mendel et al., *Annu. Rev. Biophys. Biomol. Struct.* (1995) 24:435-462, Hohsaka et al., *FEBS Lett*. (2004) 560:173-177) have been demonstrated expementally, but afford limited yields of protein and are typically carried out only in vitro.

The incorporation of genetically encoded fluorescent amino acids at defined sites in proteins directly in living organisms would overcome many of the limitations in fluorescence labeling of proteins (Wang and Schultz, *Angew. Chem. Int. Ed*. (2005) 44:34-66; Wang et al., *Annu. Rev. Biophys. Biomol. Struct*., (2006) 35:225-249). The site-specific incorporation of fluorescent amino acids would introduce minimum perturbation to the host protein and permit the measurement of fluorescence resonance energy transfer (FRET) with much greater precision (Truong and Ikura, *Curr. Opin. Struct. Bio.* 2001, 11:573-578). In addition, the use of a fluorescent amino acid will permit the probing of the local environment of each amino acid position, and pinpoint residues that mediate interaction with other cellular components by varying the position of the fluorescent amino acid in the protein. This would also be very useful to study protein folding (Lakowicz, Principles of Fluorescence Spectroscopy Ed. 2; Kluwer Academic/Plenum Publishers: New York, 1999), especially in a single-molecular system (Lipman et al., *Science* (2003) 301:1233-1235), because one protein molecule normally contains more than one tryptophan residue, and specific chemical labeling of proteins with fluorescent probes is problematic.

What are needed in the art are new strategies for incorporation of fluorescent unnatural amino acids into proteins for the purpose of studying protein structure and function. A general methodology has been developed for the in vivo site-specific incorporation of diverse unnatural amino acids into proteins in both prokaryotic and eukaryotic organisms. These methods rely on orthogonal protein translation components that recognize a suitable selector codon to insert a desired unnatural amino acid at a defined position during polypeptide translation in vivo. These methods utilize an orthogonal tRNA (O-tRNA) that recognizes a selector codon, and where a corresponding specific orthogonal aminoacyl-tRNA synthetase (an O-RS) charges the O-tRNA with the unnatural amino acid. These components do not cross-react with any of the endogenous tRNAs, RSs, amino acids or codons in the host organism (i.e., it must be orthogonal). The use of such orthogonal tRNA-RS pairs has made it possible to genetically encode a large number of structurally diverse unnatural amino acids.

The practice of using orthogonal translation systems that are suitable for making proteins that comprise one or more unnatural amino acid is generally known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 20051019415, filed Jul. 7, 2004; WO 2005/007870, filed Jul. 7, 2004; WO 20051007624, filed Jul. 7, 2004 and WO 2006/110182, filed Oct. 27, 2005, entitled "ORTHOGONAL TRANSLATION COMPONENTS FOR THE IN VIVO INCORPORATION OF UNNATURAL AMINO ACIDS." Each of these applications is incorporated herein by reference in its entirety. For additional discussion of orthogonal translation systems that incorporate unnatural amino acids, and methods for their production and use, see also, Wang and Schultz, "Expanding the Genetic Code," *Chem. Commun. (Camb.)* 1:1-11 (2002); Wang and Schultz "Expanding the Genetic Code," *Angewandre Chemie Int. Ed.,* 44(1):34-66 (2005); xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); Wang et al., "Expanding the Genetic Code," *Annu. Rev. Biophys. Biomol. Struct.,* 35:225-249 (2006); and Xie and Schultz, "A chemical toolkit for proteins—an expanded genetic code," *Nat. Rev. Mol. Cell Biol.,* 7(10):775-782 (2006), the contents of which are each incorporated by reference in their entirety.

There is a need in the art for the development of orthogonal translation components that incorporate fluorescent unnatural amino acids into proteins, where the fluorescent unnatural amino acids can be incorporated at defined positions. The invention described herein fulfills these and other needs, as will be apparent upon review of the following disclosure.

SUMMARY OF THE INVENTION

The invention provides compositions and methods for incorporating the coumarin unnatural amino acid L-(7-hydroxycoumarin-4-yl)ethylglycine into a growing polypeptide chain in response to a selector codon, e.g., an amber stop codon, in vivo (e.g., in a host cell). These compositions include pairs of orthogonal-tRNAs (O-tRNAs) and orthogonal aminoacyl-tRNA synthetases (O-RSs) that do not interact with the host cell translation machinery. That is to say, the O-tRNA is not charged (or not charged to a significant level) with an amino acid (natural or unnatural) by an endogenous host cell aminoacyl-tRNA synthetase. Similarly, the O-RSs provided by the invention do not charge any endogenous tRNA with an amino acid (natural or unnatural) to a significant or detectable level. These novel compositions permit the production of large quantities of proteins having translationally incorporated L-(7-hydroxycoumarin-4-yl)ethylglycine. These fluorescent labeled proteins find a wide variety of uses.

In some aspects, the invention provides translation systems. These systems comprise a first orthogonal aminoacyl-tRNA synthetase (O-RS), a first orthogonal tRNA (O-tRNA), and a first unnatural amino acid that is L-(7-hydroxycoumarin-4-yl)ethylglycine, where the first O-RS preferentially aminoacylates the first O-tRNA with the first unnatural amino acid.

The translation systems can use components derived from a variety of sources. In one embodiment, the first O-RS is derived from a *Methanococcus jannaschii* aminoacyl-tRNA synthetase, e.g., a wild-type *Methanococcus jannaschii* tyrosyl-tRNA synthetase. The O-RS used in the system can comprise the amino acid sequence of SEQ ID NO: 4, and conservative variants of that sequence. In some embodiments, the O-tRNA is an amber suppressor tRNA. In some embodiments, the O-tRNA comprises or is encoded by SEQ ID NO: 1.

In some aspects, the translation system further comprises a nucleic acid encoding a protein of interest, where the nucleic acid has at least one selector codon that is recognized by the O-tRNA.

In some aspects, the translation system incorporates a second orthogonal pair (that is, a second O-RS and a second O-tRNA) that utilizes a second unnatural amino acid, so that the system is now able to incorporate at least two different unnatural amino acids at different selected sites in a polypeptide. In this dual system, the second O-RS preferentially aminoacylates the second O-tRNA with a second unnatural amino acid that is different from the first unnatural amino acid, and the second O-tRNA recognizes a selector codon that is different from the selector codon recognized by the first O-tRNA.

In some embodiments, the translation system resides in a host cell (and includes the host cell). The host cell used in not particularly limited, as long as the O-RS and O-tRNA retain their orthogonality in their host cell environment. The host cell can be a eubacterial cell, such as *E. Coli*. The host cell can comprise one or more polynucleotides that encode components of the translation system, including the O-RS or O-tRNA. In some embodiments, the polynucleotide encoding the O-RS comprises a nucleotide sequence of SEQ ID NO: 5.

The invention also provides methods for producing proteins having one or more unnatural amino acids at selected positions. These methods utilize the translation systems described above. Generally, these methods start with the step of providing a translation system comprising: (i) a first unnatural amino acid that is the coumarin amino acid L-(7-hydroxycoumarin-4-yl)ethylglycine; (ii) a first orthogonal aminoacyl-tRNA synthetase (O-RS); (iii) a first orthogonal tRNA (O-tRNA), wherein the O-RS preferentially aminoacylates the O-tRNA with the unnatural amino acid; and, (iv) a nucleic acid encoding the protein, where the nucleic acid comprises at least one selector codon that is recognized by the first O-tRNA. The method then incorporates the unnatural amino acid at the selected position in the protein during translation of the protein in response to the selector codon, thereby producing the protein comprising the unnatural amino acid at the selected position.

This methods can be widely applied using a variety of reagents and steps. In some embodiments, a polynucleotide encoding the O-RS is provided. In some embodiments, an O-RS derived from a *Methanococcus jannaschii* aminoacyl-tRNA synthetase is provided, for example, a wild-type *Methanococcus jannaschii* tyrosyl-tRNA synthetase can be provided. In some embodiments, the providing step includes providing an O-RS comprising an amino acid sequence of SEQ ID NO: 4, and conservative variants thereof.

In some embodiments of these methods, the providing a translation system step comprises mutating an amino acid binding pocket of a wild-type aminoacyl-tRNA synthetase by site-directed mutagenesis, and selecting a resulting O-RS that preferentially aminoacylates the O-tRNA with the unnatural amino acid. The selecting step can comprises positively selecting and negatively selecting for the O-RS from a pool of resulting aminoacyl-tRNA synthetase molecules following site-directed mutagenesis. In some embodiments, the providing step furnishes a polynucleotide encoding the O-tRNA, e.g., an O-tRNA that is an amber suppressor tRNA, or an O-tRNA that comprises or is encoded by a polynucleotide of SEQ ID NO: 1. In these methods, the providing step can also furnish a nucleic acid comprising an amber selector codon that is utilized by the translation system.

These methods can also be modified to incorporate more than one unnatural amino acid into a protein. In those methods, a second orthogonal translation system is employed in conjunction with the first translation system, where the second system has different amino acid and selector codon specificities. For example, the providing step can include providing a second O-RS and a second O-tRNA, where the second O-RS preferentially aminoacylates the second O-tRNA with a second unnatural amino acid that is different from the first unnatural amino acid, and where the second O-tRNA recognizes a selector codon in the nucleic acid that is different from the selector codon recognized by the first O-tRNA.

The methods for producing a protein with an unnatural amino acid can also be conducted in the context of a host cell. In these cases, a host cell is provided, where the host cell comprises the unnatural amino acid, the O-RS, the O-tRNA and the nucleic acid with at least one selector codon that encodes the protein, and where culturing the host cell results in incorporating the unnatural amino acid. In some embodiments, the providing step comprises providing a eubacterial host cell (e.g., *E. coli*). In some embodiments, the providing step includes providing a host cell that contains a polynucleotide encoding the O-RS. For example, the polynucleotide encoding the O-RS can comprise a nucleotide sequence of SEQ ID NO: 5. In some embodiments, the step of providing a translation system is accomplished by providing a cell extract.

The invention also provides a variety of compositions, including nucleic acids and proteins. The nature of the composition is not particularly limited, other than the composition comprises the specified nucleic acid or protein. The compositions of the invention can comprise any number of additional components of any nature.

For example, the invention provides compositions comprising O-RS polypeptides, where the polypeptides comprise the amino acid sequence of SEQ ID NO: 4, or a conservative variant thereof, where the conservative variant polypeptide aminoacylates a cognate orthogonal tRNA (O-tRNA) with an unnatural amino acid with an efficiency that is at least 50% of the efficiency observed for a translation system comprising the O-tRNA, the unnatural amino acid, and an aminoacyl-tRNA synthetase comprising the amino acid sequence of SEQ ID NO: 4. The invention also provides polynucleotides that encode any of these polypeptides above. In some embodiments, these polynucleotides can comprise a nucleotide sequence of SEQ ID NO: 5. In some embodiments, the polypeptides are in a cell.

The invention also provides polynucleotide compositions comprising a nucleotide sequence of SEQ ID NO: 5. In some embodiments, the invention provides vectors comprising the polynucleotides, e.g., expression vectors. In some embodiments, the invention provides cells comprising a vector described above.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any example tRNA that is designated as a substrate for a tyrosyl-tRNA synthetase in FIG. 9, or (6) a conservative variant of any example tRNA that is designated as a substrate for a tyrosyl-tRNA synthetase in FIG. 9. The tyrosyl-tRNA can exist charged with an amino acid, or in an uncharged state. It is also to be understood that a "tyrosyl-O-tRNA" optionally is charged (aminoacylated) by a cognate synthetase with an amino acid other than tyrosine, respectively, e.g., with an unnatural amino acid. Indeed, it will be appreciated that a tyrosyl-O-tRNA of the invention is advantageously used to insert essentially any amino acid, whether natural or unnatural, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS in FIG. 9. For example, the O-RS can be a conservative variant of a tyrosyl-O-RS of FIG. 9, and/or can be at least 50%, 60%, 70%, 80%, 90%, 95%, 98%, 99% or more identical in sequence to an O-RS of FIG. 9.

Cognate: The term "cognate" refers to components that function together, or have some aspect of specificity for each other, e.g., an orthogonal tRNA and an orthogonal aminoacyl-tRNA synthetase. The components can also be referred to as being complementary.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, typically by allowing the incorporation of an amino acid in response to a stop codon (i.e., "read-through") during the translation of a polypeptide. In some aspects, a selector codon of the invention is a suppressor codon, e.g., a stop codon (e.g., an amber, ocher or opal codon), a four base codon, a rare codon, etc.

Suppression activity: As used herein, the term "suppression activity" refers, in general, to the ability of a tRNA (e.g., a suppressor tRNA) to allow translational read-through of a codon (e.g., a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various methods by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluorm™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as E. coli), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, that is not one of the 20 common naturally occurring amino acids or seleno cysteine or pyrrolysine. For example, the unnatural amino acid L-(7-hydroxycoumarin-4-yl)ethylglycine (also written 7-hydroxycoumarin-ethylglycine; see FIG. 1, structure 1) finds use with the invention.

Derived from: As used herein, the term "derived from" refers to a component that is isolated from or made using a specified molecule or organism, or information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Positive selection or screening marker: As used herein, the term "positive selection or screening marker" refers to a marker that, when present, e.g., expressed, activated or the like, results in identification of a cell, which comprises the trait, e.g., a cell with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokarvote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Bacteria: As used herein, the terms "bacteria" and "eubacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans and other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus thermophilus, Bacillus subtilis* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Ap), *Pyrococcus furiosus* (Pf), *Pyrococcus horikoshii* (Ph), *Pyrobaculum aerophilun, Pyrococcus abyssi, Sulfolobus solfataricus* (Ss), *Sulfolobus tokodaii, Aeuropyrum pernix* (Ap), *Thermoplasma acidophilum* and *Thermoplasma volcanium*.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS, or a conservative variant of that O-RS, will aminoacylate a cognate O-tRNA with an unnatural amino acid, e.g., an L-(7-hydroxycoumarin-4-yl)ethylglycine unnatural amino acid. In this example, the O-RS and the conservative variant O-RS do not have the same amino acid sequences. The conservative variant can have, e.g., one variation, two variations, three variations, four variations, or five or more variations in sequence, as long as the conservative variant is still complementary to (e.g., functions with) the cognate corresponding O-tRNA or O-RS.

In some embodiments, a conservative variant O-RS comprises one or more conservative amino acid substitutions compared to the O-RS from which it was derived. In some embodiments, a conservative variant O-RS comprises one or more conservative amino acid substitutions compared to the O-RS from which it was derived, and furthermore, retains O-RS biological activity; for example, a conservative variant O-RS that retains at least 10% of the biological activity of the parent O-RS molecule from which it was derived, or alternatively, at least 20%, at least 30%, or at least 40%. In some preferred embodiments, the conservative variant O-RS retains at least 50% of the biological activity of the parent O-RS molecule from which it was derived. The conservative amino acid substitutions of a conservative variant O-RS can occur in any domain of the O-RS, including the amino acid binding pocket.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semiconservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 9 provides various nucleotide and amino acid sequences.

DETAILED DESCRIPTION OF THE INVENTION

The present specification provides orthogonal tRNA/aminoacyl-tRNA synthetase pairs that allow the in vivo selective introduction of the fluorescent amino acid L-(7-hydroxycoumarin-4-yl)ethylglycine (see FIG. 1, structure 1) into proteins in *E. coli* in response to a selector codon, e.g., the amber stop codon TAG. The invention provides novel orthogonal aminoacyl-tRNA synthetase (O-RS) polypeptides that specifically charge a cognate orthogonal tRNA (O-tRNA) with the unnatural amino acid L-(7-hydroxycoumarin-4-yl)ethylglycine.

Figure 2:
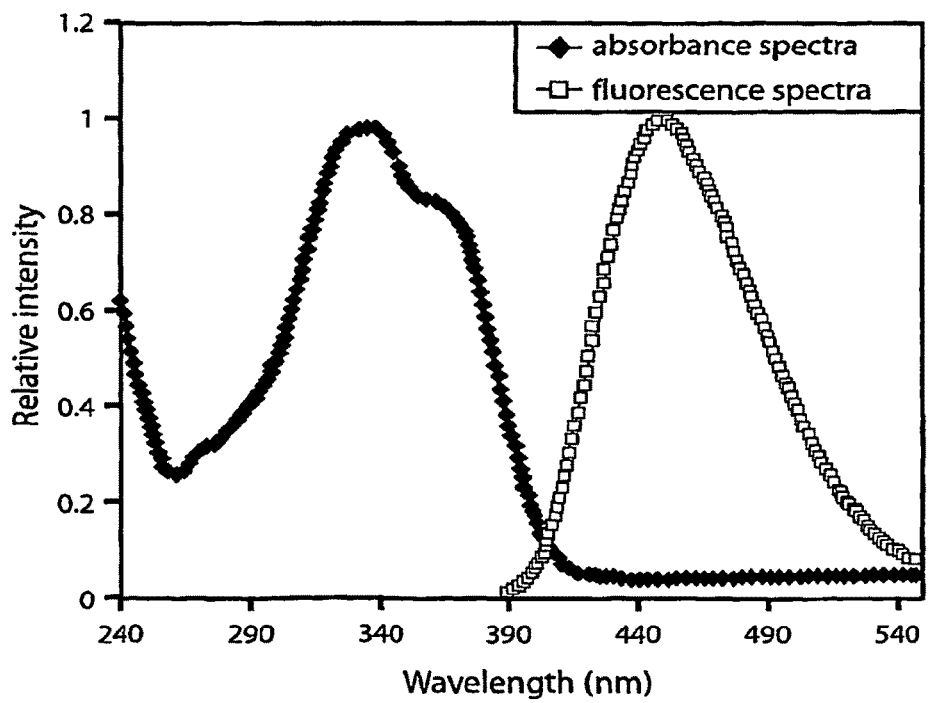
FIG. 2 provides absorption and emission spectra of L-(7-hydroxycoumarin-4-yl)ethylglycine. Both spectra were recorded at pH 7.4, 100 mM sodium phosphate buffer. At this pH, L-(7-hydroxycoumarin-4-yl)ethylglycine is present in both phenol and phenolate forms (in approximately a 2:1 ratio). The phenolate form has an extinction coefficient of 17000 at 360 nM and a quantum yield of 0.63.

The 7-hydroxycoumarin moiety was initially investigated due to its high fluorescence quantum yield, relatively large Stoke's shift (see FIG. 2), small size, sensitivity to pH (see FIG. 7) and solvent polarity (Zinsli, *J. Photochem* (1974) 3:55-69).

In some aspects, to demonstrate (but not to limit) the present invention, the disclosure herein demonstrates that the unnatural amino acid moiety can be incorporated into a model protein (see EXAMPLES 4 and 5). It is not intended that the incorporation of the unnatural amino acid be limited to any particular protein. From the present disclosure, it will be clear that the incorporation of the unnatural fluorescent amino acid into a particular protein of interest is advantageous for a wide variety of purposes.

Figure 1:
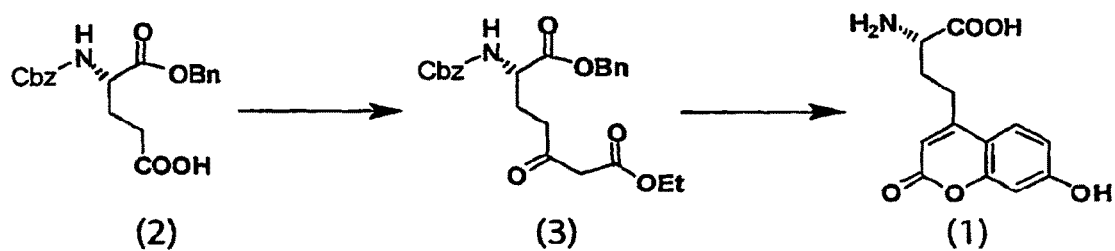
FIG. 1 provides a schematic of the chemical synthesis of L-(7-hydroxycoumarin-4-yl)ethylglycine (structure 1).

The present disclosure describes the evolution of novel orthogonal tRNA/aminoacyl-tRNA synthetase pairs that function in eubacteria to site specifically incorporate an unnatural fluorescent amino acid (e.g., the unnatural amino acid L-(7-hydroxycoumarin-4-yl)ethylglycine provided in FIG. 1, structure 1) in response to selector codons. Briefly, we have identified novel mutants of the *Methanococcus jannaschii* tyrosyl-tRNA synthetase that selectively charge a suppressor tRNA with the unnatural amino acid in *E. coli* host cells.

These evolved tRNA-synthetase pairs can be used to site-specifically incorporate the unnatural fluorescent amino acid into a protein. The incorporation of the unnatural amino acid into the protein can be programmed to occur at any desired position by engineering the polynucleotide encoding the protein of interest to contain a selector codon that signals the incorporation of the unnatural amino acid.

The invention described herein provides orthogonal pairs for the genetic encoding and incorporation of an L-(7-hydroxycoumarin-4-yl)ethylglycine unnatural amino acid into proteins in a eubacteria, e.g., an *E. coli* cell, where the orthogonal components do not cross-react with endogenous *E. coli* components of the translational machinery of the host cell, but recognize the desired unnatural amino acid and incorporate it into proteins in response to a selector codon (e.g., an amber nonsense codon, TAG). The orthogonal components provided by the invention include orthogonal aminoacyl-tRNA synthetases derived from *Methanococcus jannaschii* tyrosyl tRNA-synthetase, and the mutant tyrosyl tRNA$_{CUA}$ amber suppressor, which function as an orthogonal pair in a eubacterial host cell.

This invention provides compositions of and methods for identifying and producing additional orthogonal tRNA-aminoacyl-tRNA synthetase pairs, e.g., O-tRNA/O-RS pairs that can be used to incorporate the L-(7-hydroxycoumarin-4-yl) ethylglycine unnatural amino acid into a protein. An O-tRNA/O-RS pair of the invention is capable of mediating incorporation of the 7-hydroxycoumarin-ethylglycine into a protein that is encoded by a polynucleotide, where the polynucleotide comprises a selector codon that is recognized by the O-tRNA. The anticodon loop of the O-tRNA recognizes the selector codon on an mRNA and incorporates the unnatural amino acid at this site in the polypeptide. Generally, an orthogonal aminoacyl-tRNA synthetase of the invention preferentially aminoacylates (or charges) its O-tRNA with only one specific unnatural amino acid.

Orthogonal tRNA/Aminoacyl-tRNA Synthetase Technology

An understanding of the novel compositions and methods of the present invention requires an understanding of the activities associated with orthogonal tRNA and orthogonal aminoacyl-tRNA synthetase pairs. In order to add additional unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthogonal pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated (or is poorly aminoacylated, i.e., charged) by endogenous synthetases. For example, in an *E. coli* host system, an orthogonal pair will include an aminoacyl-tRNA synthetase that does not cross-react with any of the endogenous tRNA, e.g., which there are 40 in *E. coli*, and an orthogonal tRNA that is not aminoacylated by any of the endogenous synthetases, e.g., of which there are 21 in *E. coli*.

The general principles of orthogonal translation systems that are suitable for making proteins that comprise one or more unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE IN VIVO INCORPORATION OF UNNATURAL AMINO ACIDS," and U.S. Utility application Ser. No. 11/715,672, entitled "SYSTEMS FOR THE EXPRESSION OF ORTHOGONAL TRANSLATION COMPONENTS IN EUBACTERIAL HOST CELLS," filed Mar. 7, 2007. Each of these applications is incorporated herein by reference in its entirety. For discussion of orthogonal translation systems that incorporate unnatural amino acids, and methods for their production and use, see also, Wang and Schultz, "Expanding the Genetic Code," *Chem. Commun. (Camb.)* 1:1-11 (2002); Wang and Schultz "Expanding the Genetic Code," *Angewandte Chemie Int. Ed.*, 44(1):34-66 (2005); Xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); Wang et al., "Expanding the Genetic Code," *Annu. Rev. Biophys. Biomol. Struct.*, 35:225-249 (2006); and Xie and Schultz, "A chemical toolkit for proteins—an expanded genetic code," *Nat. Rev. Mol. Cell Biol.*, 7(10):775-782 (2006), the contents of which are each incorporated by reference in their entirety.

Orthogonal Translation Systems

Orthogonal translation systems generally comprise cells (which can be prokaryotic cells such as *E. coli*) that include an orthogonal tRNA (O-tRNA), an orthogonal aminoacyl tRNA synthetase (O-RS), and an unnatural amino acid, where the O-RS aminoacylates the O-tRNA with the unnatural amino acid. An orthogonal pair of the invention can include an O-tRNA, e.g., a suppressor tRNA, a frameshift tRNA, or the like, and a cognate O-RS. The orthogonal systems of the invention can typically comprise O-tRNA/O-RS pairs, either in the context of a host cell or without the host cell. In addition to multi-component systems, the invention also provides novel individual components, for example, novel orthogonal aminoacyl-tRNA synthetase polypeptides (e.g., SEQ ID NO: 4), and the polynucleotides that encodes those polypeptides (e.g., SEQ ID NO: 5).

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily charged, which results in blocking production of a polypeptide that would otherwise be translated from the nucleic acid. In an orthogonal pair system, the O-RS aminoacylates the O-tRNA with a specific unnatural amino acid. The charged O-tRNA recognizes the selector codon and suppresses the translational block caused by the selector codon.

In some aspects, an O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to the suppression efficiency of an O-tRNA comprising or encoded by a polynucleotide sequence as set forth in the sequence listing herein.

In some embodiments, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In some aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

The host cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain preferred aspects, the cell can include one or more additional O-tRNA/O-RS pairs, where the additional O-tRNA is loaded by the additional O-RS with a different unnatural amino acid. For example, one of the O-tRNAs can recognize a four base codon and the other O-tRNA can recognize a stop codon. Alternately, multiple different stop codons or multiple different four base codons can be used in the same coding nucleic acid.

As noted, in some embodiments, there exists multiple O-tRNA/O-RS pairs in a cell or other translation system, which allows incorporation of more than one unnatural amino acid into a polypeptide. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, where the second O-tRNA recognizes a different selector codon, e.g., an opal codon, a four-base codon, or the like. Desirably, the different orthogonal pairs are derived from different sources, which can facilitate recognition of different selector codons.

In certain embodiments, systems comprise a cell such as an *E. coli* cell that includes an orthogonal tRNA (O-tRNA), an orthogonal aminoacyl-tRNA synthetase (O-RS), an unnatural amino acid and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/O-RS pair and an unnatural amino acid as described herein.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases. A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention desirably mediates incorporation of an unnatural amino acid into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Examples of O-tRNAs of the invention are set forth in the sequence listing herein, for example, see FIG. 9 and SEQ ID NO: 1. The disclosure herein also provides guidance for the design of additional equivalent O-tRNA species. In an RNA molecule, such as an O-RS mRNA, or O-tRNA molecule, thymine (T) is replace with uracil (U) relative to a given sequence (or vice versa for a coding DNA), or complement thereof. Additional modifications to the bases can also be present to generate largely functionally equivalent molecules.

The invention also encompasses conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing or FIG. 9, and desirably, are other than wild type tRNA molecules.

The composition comprising an O-tRNA can further include an orthogonal aminoacyl-tRNA synthetase (O-RS), where the O-RS preferentially aminoacylates the O-tRNA with an unnatural amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell.

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof, e.g., of the O-tRNA of SEQ ID NO: 1.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding additional sequences to the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in E. coli, a synthetase and/or a tRNA is chosen that does not display close sequence similarity to eubacterial organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense (e.g., stop) or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous E. coli synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., Escherichia coli synthetases (i.e., it is not orthogonal to the host, e.g., Escherichia coli synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., Escherichia coli, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In some aspects of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that loads an unnatural amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco et al., (1993) "Production and fluorescence-activated cell sorting of *Escherichia coli* expressing a functional antibody fragment on the external surface," *Proc Natl Acad Sci USA*. 90:10444-10448.

Additional methods for producing a recombinant orthogonal tRNA can be found, e.g., in International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) "Programming peptidomimetic synthetases by translating genetic codes designed de novo," *PNAS* 100(11):6353-6357; and, Peng et al., (2003), "Expanding tRNA recognition of a tRNA synthetase by a single amino acid change," PNAS 100(10):5676-5681.

Orthogonal Aminoacyl-tRNA Synthetase (O-RS)

An O-RS of the invention preferentially aminoacylates an O-tRNA with an unnatural amino acid, in vitro or in vivo. An O-RS of the invention can be provided to the translation system, e.g., a cell, by a polypeptide that includes an O-RS and/or by a polynucleotide that encodes an O-RS or a portion thereof. For example, an example O-RS comprises an amino acid sequence as set forth in SEQ ID NO: 4, or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See, e.g., the polynucleotide of SEQ ID NO: 5.

Methods for identifying an orthogonal aminoacyl-tRNA synthetase (O-RS), e.g., an O-RS, for use with an O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled unnatural amino acid). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O-RS can be further manipulated to alter substrate specificity of the synthetase, so that only a desired unnatural amino acid, but not any of the common 20 amino acids, are charged to the O-tRNA. Methods to generate an orthogonal aminoacyl-tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al.; U.S. Pat. No. 5,756,316 to Schallenberger et al.; U.S. Pat. No. 5,783,431 to Petersen et al.; U.S. Pat. No. 5,824,485 to Thompson et al.; U.S. Pat. No. 5,958,672 to Short et al.), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid. In some aspects of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE." See also, Wang and Schultz "Expanding the Genetic Code," *Angewandte Chemie Int. Ed.*, 44(1):34-66 (2005), the content of which is incorporated by reference in its entirety.

Source and Host Organisms

The orthogonal translational components (O-tRNA and O-RS) of the invention can be derived from any organism (or a combination of organisms) for use in a host translation system from any other species, with the caveat that the O-tRNA/O-RS components and the host system work in an orthogonal manner. It is not a requirement that the O-tRNA and the O-RS from an orthogonal pair be derived from the same organism. In some aspects, the orthogonal components are derived from Archaea genes (i.e., archaebacteria) for use in a eubacterial host system.

For example, the orthogonal O-tRNA can be derived from an Archae organism, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandlern, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thernus thermophilus, Bacillus subtilis, Bacillus stearothennphilus*, or the like, while the orthogonal O-RS can be derived from an organism or combination of organisms, e.g., an archaebacterium, such as *Methanococcus jannaschii, Methanobacterium thernoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina muazei, Pyrobaculum aerophilum, Pyrococcus abyssi, Sulfolobus solfataricus, Sulfolobus tokodaii, Thermoplasma acidophilum, Thermoplasma volcanium*, or the like, or a *eubacterium*, such as *Escherichia coli, Thermus thernophilus, Bacillus subtilis, Bacillus stearothemmphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a eubacterial cell, to produce a polypeptide with an unnatural amino acid. The eubacterial cell used is not limited, for example, *Escherichia coli, Thermus thermophilus, Bacillus subtilis, Bacillus stearothernophilus*, or the like. Compositions of eubacterial cells comprising translational components of the invention are also a feature of the invention.

See also, International Publication Number WO 2004/094593, entitled "EXPANDING THE EUKARYOTIC GENETIC CODE," filed Apr. 16, 2004, for screening O-tRNA and/or O-RS in one species for use in another species.

Although orthogonal translation systems (e.g., comprising an O-RS, an O-tRNA and an unnatural amino acid) can utilize cultured host cells to produce proteins having unnatural amino acids, it is not intended that an orthogonal translation system of the invention require an intact, viable host cell. For example, a orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one unnatural amino acid, using these different selector codons.

In one embodiment, the methods involve the use of a selector codon that is a stop codon for the incorporation of an unnatural amino acid in vivo in a cell. For example, an O-tRNA is produced that recognizes the stop codon and is aminoacylated by an O-RS with an unnatural amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers et al. (1988), "5',3' Exonuclease in phosphorothioate-based oligonucleotide-directed mutagenesis," *Nucleic Acids Res*, 791-802. When the O-RS, O-tRNA and the nucleic acid that encodes a polypeptide of interest are combined, e.g., in vivo, the unnatural amino acid is incorporated in response to the stop codon to give a polypeptide containing the unnatural amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of unnatural amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1)

(which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothreitol (DTT).

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al. (1993), *Biochemistry* 32:7939. In this case, the synthetic tRNA competes with the naturally occurring tRNA$^{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver (1997), *Nucl. Acid. Res.,* 25:4685. Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) "Exploring the Limits of Codon and Anticodon Size," *Chemistry and Biology,* 9:237-244; and, Magliery, (2001) "Expanding the Genetic Code: Selection of Efficient Suppressors of Four-base Codons and Identification of "Shifty" Four-base Codons with a Library Approach in *Escherichia coli,*" *J. Mol. Biol.,* 307:755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense readthrough and frameshift suppression at other unwanted sites. Four base codons have been used as selector codons in a variety of orthogonal systems. See, e.g., WO 2005/019415; WO 2005/007870 and WO 2005/07624. See also, Wang and Schultz "Expanding the Genetic Code," *Angewandte Chemie Int. Ed.,* 44(1):34-66 (2005), the content of which is incorporated by reference in its entirety. While the examples below utilize an amber selector codon, four or more base codons can be used as well, by modifying the examples herein to include four-base O-tRNAs and synthetases modified to include mutations similar to those previously described for various unnatural amino acid O-RSs.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao et al., (2002) "An unnatural base pair for incorporating amino acid analogues into protein," *Nature Biotechnology,* 20:177-182. See also Wu et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3M self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also beendeveloped, which forms a stable pair upon binding Cu(II). See Meggers et al., (2000) *J. Am. Chem. Soc.*, 122: 10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

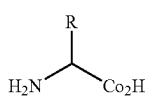

I

An unnatural amino acid is typically any structure having Formula I wherein the R group is any substituent other than one used in the twenty natural amino acids. See e.g., *Biochemistry* by L. Stryer, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest herein is the unnatural coumarin amino acid L-(7-hydroxycoumarin-4-yl)ethylglycine (also written 7-hydroxycoumarin-ethylglycine; see FIG. 1, structure 1). In addition to the 7-hydroxycoumarin-ethylglycine unnatural amino acid, other unnatural amino acids can be simultaneously incorporated into a polypeptide of interest, e.g., using an appropriate second O-RS/O-tRNA pair in conjunction with an orthogonal pair provided by the present invention. Many such additional unnatural amino acids and suitable orthogonal pairs are known. See the present disclosure and the references cited herein. For example, see Wang and Schultz "Expanding the Genetic Code," *Angewandte Chemie Int. Ed.*, 44(1):34-66 (2005); xie and Schultz, "An Expanding Genetic Code," *Methods* 36(3):227-238 (2005); Xie and Schultz, "Adding Amino Acids to the Genetic Repertoire," *Curr. Opinion in Chemical Biology* 9(6):548-554 (2005); and Wang et al., "Expanding the Genetic Code," *Annu. Rev. Biophys. Biomol. Struct.*, 35:225-249 (2006); the contents of which are each incorporated by reference in their entirety.

Although the unnatural coumarin amino acid L-(7-hydroxycoumarin-4-yl)ethylglycine (shown in FIG. 1, structure 1) is of primary interest in the Examples described herein, it is not intended that the invention be strictly limited to that structure. Indeed, a variety of easily-derived, structurally related analogs can be readily produced that retain the principle characteristic of fluorescence, and also are specifically recognized by the aminoacyl-tRNA synthetases of the invention (e.g., the O-RS of SEQ ID NO: 4). It is intended that these related fluorescent analogues are within the scope of the invention.

In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photo-cleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides unnatural amino acids having the general structure illustrated by Formula IV below:

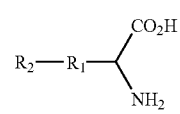

IV

An unnatural amino acid having this structure is typically any structure where $R_1$ is a substituent used in one of the twenty natural amino acids (e.g., tyrosine or phenylalanine) and $R_2$ is a substituent. Thus, this type of unnatural amino acid can be viewed as a natural amino acid derivative.

In addition to unnatural amino acids that contain the coumarin side chain such as shown in FIG. 1, structure 1, unnatu ral amino acids can also optionally comprise modified backbone structures, e.g., as illustrated by the structures of Formula II and III:

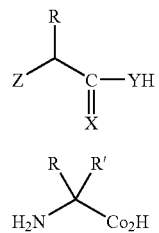

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

In some aspects, the invention utilizes unnatural amino acids in the L configuration. However, it is not intended that the invention be limited to the use of L-configuration unnatural amino acids. It is contemplated that the D-enantiomers of these unnatural amino acids also find use with the invention.

The unnatural amino acids finding use with the invention is not strictly limited to the coumarin unnatural amino acid L-(7-hydroxycoumarin-4-yl)ethylglycine. One of skill in the art will recognize that a wide variety of unnatural analogs of naturally occurring amino acids are easily derived. For example, but not limited to, unnatural derived from tyrosine are readily produced. Tyrosine analogs include, e.g., para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a C$_6$-C$_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenylalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, p-eth-ylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenyl alanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenyalanine (DHP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are disclosed in the references cited herein. See also, International Publications WO 2004/094593, entitled "EXPANDING THE EUKARYOTIC GENETIC CODE;" and WO 2006/110182, filed Oct. 27, 2005, entitled "ORTHOGONAL TRANSLATION COMPONENTS FOR THE IN VIVO INCORPORATION OF UNNATURAL AMINO ACIDS."

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 20021085923 entitled "IN VIVO INCORPORATION OF UNNATURAL AMINO ACIDS," Matsoukas et al., (1995) *J. Med. Chem.,* 38:4660-4669; King and Kidd (1949) "A New Synthesis of Glutamine and of γ-Dipeptides of Glutamic Acid from Phthylated Intermediates," *J. Chem. Soc.,* 3315-3319; Friedman and Chatterrji (1959) "Synthesis of Derivatives of Glutamine as Model Substrates for Anti-Tumor Agents," *J. Am. Chem. Soc.* 81:3750-3752; Craig et al. (1988) "Absolute Configuration of the Enantiomers of 7-Chloro-4 [[4-(diethylamino)-1-methylbutyl]amino]quinoline (Chloroquine)," *J. Org. Chem.* 53:1167-1170; Azoulay et al., (1991) "Glutamine analogues as Potential Antimalarials," *Eur. J. Med. Chem.* 26:201-205; Koskinen and Rapoport, (1989) "Synthesis of 4-Substituted Prolines as Conformationally Constrained Amino Acid Analogues," *J. Org. Chem.* 54:1859-1866; Christie and Rapoport (1985) "Synthesis of Optically Pure Pipecolates from L-Asparagine. Application to the Total Synthesis of (+)-Apovincamine through Amino Acid Decarbonylation and Iminium Ion Cyclization," *J. Org. Chem.* 1989: 1859-1866; Barton et al., (1987) "Synthesis of Novel α-Amino-Acids and Derivatives Using Radical Chemistry: Synthesis of L- and D-α-Amino-Adipic Acids, L-α-aminopimelic Acid and Appropriate Unsaturated Derivatives," *Tetrahedron Lett.* 43:4297-4308; and, Subasinghe et al., (1992) "Quisqualic acid analogues: synthesis of beta-heterocyclic 2-aminopropanoic acid derivatives and their activity at a novel quisqualate-sensitized site," *J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) "Progress toward the evolution of an organism with an expanded genetic code," PNAS 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), "Rapid evolution of a protein in vitro by DNA shuffling," *Nature* 370(4):389-391; and, Stemmer, (1994) "DNA shuffling by random fragmentation and reassembly: In vitro recombination for molecular evolution," *Proc. Natl. Acad ScL USA.*, 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave and Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology,* 20(7): 707-712; and Zhang et al. (2002) "Genome shuffling leads to rapid phenotypic improvement in bacteria" *Nature*, February 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.*

14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of *Corynebacterium* 2,5-diketo-D-gluconic acid reductase for use in vitamin C biosynthesis" *Biochemistry*, 41(20), 6226-36; Selivonova et al. (2001) "Rapid Evolution of Novel Traits in Microorganisms" *Applied and Environmental Microbiology*, 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Unnatural Amino Acids

The invention provides compositions and methods for producing orthogonal components for incorporating the unnatural amino acid L-(7-hydroxycoumarin-4-yl)ethylglycine (see FIG. 1, structure 1) into a growing polypeptide chain in response to a selector codon, e.g., an amber stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate an unnatural amino acid into growing polypeptide chains.

A composition of the invention includes an orthogonal aminoacyl-tRNA synthetase (O-RS), where the O-RS preferentially aminoacylates an O-tRNA with 7-hydroxycoumarin-ethylglycine. In certain embodiments, the O-RS comprises an amino acid sequence comprising SEQ ID NO: 4, and conservative variations thereof. In certain embodiments of the invention, the O-RS preferentially aminoacylates the O-tRNA over any endogenous tRNA with the particular unnatural amino acid, where the O-RS has a bias for the O-tRNA, and where the ratio of O-tRNA charged with an unnatural amino acid to the endogenous tRNA charged with the same unnatural amino acid is greater than 1:1, and more preferably where the O-RS charges the O-tRNA exclusively or nearly exclusively.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 1) and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA in the absence of an O-RS. In some aspects, the suppression efficiency of the O-RS and the O-tRNA together is at least 45% of the suppression efficiency of an orthogonal tyrosyl-tRNA synthetase pair derived from *Methanococcus jannaschii*.

A composition that includes an O-tRNA can optionally include a cell (e.g., a eubacterial cell, such as an *E. coli* cell and the like, or a eukaryotic cell such as a yeast cell), and/or a translation system.

A cell (e.g., a eubacterial cell or a yeast cell) comprising a translation system is also provided by the invention, where the translation system includes an orthogonal-tRNA (O-tRNA); an orthogonal aminoacyl-tRNA synthetase (O-RS); and, a 7-hydroxycoumarin-ethylglycine unnatural amino acid. Typically, the O-RS preferentially aminoacylates the O-tRNA over any endogenous tRNA with the unnatural amino acid, where the O-RS has a bias for the O-tRNA, and where the ratio of O-tRNA charged with the unnatural amino acid to the endogenous tRNA charged with the unnatural amino acid is greater than 1:1, and more preferably where the O-RS charges the O-tRNA exclusively or nearly exclusively. The O-tRNA recognizes the first selector codon, and the O-RS preferentially aminoacylates the O-tRNA with an unnatural amino acid. In one embodiment, the O-tRNA comprises or is encoded by a polynucleotide sequence as set forth in SEQ ID NO: 1, or a complementary polynucleotide sequence thereof. In one embodiment, the O-RS comprises an amino acid sequence as set forth in SEQ ID NO: 4, and conservative variations thereof.

A cell of the invention can optionally further comprise an additional different O-tRNA/O-RS pair and a second-unnatural amino acid, e.g., where this O-tRNA recognizes a second selector codon and this O-RS preferentially aminoacylates the corresponding O-tRNA with the second unnatural amino acid, where the second amino acid is different from the first unnatural amino acid. Optionally, a cell of the invention includes a nucleic acid that comprises a polynucleotide that encodes a polypeptide of interest, where the polynucleotide comprises a selector codon that is recognized by the O-tRNA.

In certain embodiments, a cell of the invention is a eubacterial cell (such as *E. coli*), that includes an orthogonal-tRNA (O-tRNA), an orthogonal aminoacyl-tRNA synthetase (O-RS), an unnatural amino acid, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with the unnatural amino acid with an efficiency that is greater than the efficiency with which the O-RS aminoacylates any endogenous tRNA.

In certain embodiments of the invention, an O-tRNA of the invention comprises or is encoded by a polynucleotide sequence as set forth in the sequence listings (e.g., SEQ ID NO: 1) or examples herein, or a complementary polynucleotide sequence thereof. In certain embodiments of the invention, an O-RS comprises an amino acid sequence as set forth in the sequence listings, or a conservative variation thereof. In one embodiment, the O-RS or a portion thereof is encoded by a polynucleotide sequence encoding an amino acid as set forth in the sequence listings or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention (e.g., SEQ ID NO: 5) includes an artificial (e.g., man-made, and not naturally occurring) polynucleotide comprising a nucleotide sequence encoding a polypeptide as set forth in the sequence listings herein, and/or is complementary to or that polynucleotide sequence. A polynucleotide of the invention can also include a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that is orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges an O-tRNA with an unnatural amino acid are also provided. For example, methods include subjecting a population of cells of a first species to a selection, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., in a eubacterial cell such as an *E. coli* cell or the like, or in a yeast cell) having the unnatural amino acid at a selected position are also a feature of the invention. For example, a method includes growing, in an appropriate medium, a cell, where the cell comprises a nucleic acid that comprises at least one selector codon and encodes a protein, providing the unnatural amino acid, and incorporating the unnatural amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. A protein produced by this method is also a feature of the invention.

The invention also provides compositions that include proteins, where the proteins comprise 7-hydroxycoumarin-ethylglycine. In certain embodiments, the protein comprises an amino acid sequence that is at least 75% identical to that of a known protein, e.g., a therapeutic protein, a diagnostic protein, an industrial enzyme, or portion thereof. Optionally, the composition comprises a pharmaceutically acceptable carrier.

Nucleic Acid and Polypeptide Sequences and Variants

As described herein, the invention provides for polynucleotide sequences encoding, e.g., O-tRNAs and O-RSs, and polypeptide amino acid sequences, e.g., O-RSs, and, e.g., compositions, systems and methods comprising said polynucleotide or polypeptide sequences. Examples of said sequences, e.g., O-tRNA and O-RS amino acid and nucleotide sequences are disclosed herein (see FIG. 9, e.g., SEQ ID NOs: 4 and 5). However, one of skill in the art will appreciate that the invention is not limited to those sequences disclosed herein, e.g., in the Examples and sequence listing. One of skill will appreciate that the invention also provides many related sequences with the functions described herein, e.g., polynucleotides and polypeptides encoding conservative variants of an O-RS disclosed herein.

The construction and analysis of orthogonal synthetase species (O-RS) that are able to aminoacylate an O-tRNA with an 7-hydroxycoumarin-ethylglycine unnatural amino acid are described in Examples 3-5. These Examples describes the construction and analysis of the O-RS species that are able to incorporate the unnatural amino acid 7-hydroxycoumarin-ethylglycine.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in SEQ ID NO: 5, and a polynucleotide that is complementary to or that encodes a polynucleotide sequence thereof. A polynucleotide of the invention also includes any polynucleotide that encodes an O-RS amino acid sequence comprising SEQ ID NO: 4. Similarly, an artificial nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide also includes an artificial polynucleotide that is, e.g., at least 75%, at least 80%, at least 90%, at least 95%, at least 98% or more identical (but not 100% identical) to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence; to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

| Conservative Amino Acid Substitutions | | | | |
|---|---|---|---|---|
| Nonpolar and/or Aliphatic Side Chains | Polar, Uncharged Side Chains | Aromatic Side Chains | Positively Charged Side Chains | Negatively Charged Side Chains |
| Glycine Alanine Valine Leucine Isoleucine Proline | Serine Threonine Cysteine Methionine Asparagine Glutamine | Phenylalanine Tyrosine Tryptophan | Lysine Arginine Histidine | Aspartate Glutamate |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to a nucleic acid represented by SEQ ID NO: 5, under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, Part I, Chapter 2, "Overview of principles of hybridization and the strategy of nucleic acid probe assays," (Elsevier, N.Y.), as well as in *Current Protocols in Molecular Biology*, Ausubel et al., eds., *Current Protocols*, a joint venture between Greene Publishing Associates, Inc. and John Wiley & Sons, Inc., (supplemented through 2006); Hames and Higgins (1995) *Gene Probes* 1, IRL Press at Oxford University Press, Oxford, England, and Hames and Higgins (1995) *Gene Probes* 2, IRL Press at Oxford University Press, Oxford, England, provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook et al., Molecular Cloning—A Laboratory Manual (3rd Ed.), Vol. 1-3, Cold Spring Harbor Laboratory, Cold Spring Harbor, N.Y., 2001, for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes*, Part I, Chapter 2, "Overview of principles of hybridization and the strategy of nucleic acid probe assays," (Elsevier, N.Y.); and Hames and Higgins (1995) *Gene Probes* 1, IRL Press at Oxford University Press, Oxford, England, and Hames and Higgins (1995) *Gene Probes* 2, IRL Press at Oxford University Press, Oxford, England. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched comple-mentary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention or related nucleic acids.

Similarly, the invention includes a polypeptide which comprises a unique subsequence in a polypeptide selected from the sequences of O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon.

When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2006).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (see the NCBI website). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold Altschul et al. (1990), *J. Mol. Biol.* 215:403-410. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, "Guide to Molecular Cloning Techniques," *Methods in Enzymology*, volume 152, Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2001 and Current Protocols in Molecular Biology, Ausubel et al., eds., *Current Protocols*, a joint venture between Greene Publishing Associates, Inc. and John Wiley & Sons, Inc., (supplemented through 2006). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode an unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman and Smith, *Gene* 8:81 (1979); Roberts, et al., *Nature*, 328:731 (1987); Schneider et al., *Protein Expr. Purif.* 6435:10 (1995); Berger and Kimmel, "Guide to Molecular Cloning Techniques," *Methods in Enzymology*, volume 152, Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2001; and *Current Protocols in Molecular Biology*, Ausubel et al., eds., *Current Protocols*, a joint venture between Greene Publishing Associates, Inc. and John Wiley & Sons, Inc., (supplemented through 2006). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82:5824 (1985), infection by viral vectors, high velocity ballistic penetration by small particles with the nucleic acid either within the matrix of small beads or particles, or on the surface (Klein et al., (1987) *Nature* 327, 70-73), and/or the like.

A highly efficient and versatile single plasmid system was developed for site-specific incorporation of unnatural amino acids into proteins in response to the amber stop codon (UAG) in *E. coli*. In the new system, the pair of *M. jannaschii* suppressor tRNAtyr(CUA) and tyrosyl-tRNA synthetase are encoded in a single plasmid, which is compatible with most *E. coli* expression vectors. Monocistronic tRNA operon under control of proK promoter and terminator was constructed for optimal secondary structure and tRNA processing. Introduction of a mutated form of glnS promoter for the synthetase resulted in a significant increase in both suppression efficiency and fidelity. Increases in suppression efficiency were also obtained by multiple copies of tRNA gene as well as by a specific mutation (D286R) on the synthetase (Kobayashi et al. (2003), "Structural basis for orthogonal tRNA specificities of tyrosyl-tRNA synthetases for genetic code expansion," *Nat. Struct. Biol.*, 10(6):425-432). The generality of the optimized system was also demonstrated by highly efficient and accurate incorporation of several different unnatural amino acids, whose unique utilities in studying protein function and structure were previously proven.

A catalogue of Bacteria and Bacteriophages useful for cloning is provided, e.g., by the ATCC, e.g., *The ATCC Catalogue of Bacteria and Bacteriophage* (1996) Ghema et al. (eds) published by the ATCC. Additional basic procedures for sequencing, cloning and other aspects of molecular biology and underlying theoretical considerations are also found in Sambrook et al., Molecular Cloning—A Laboratory Manual (3rd Ed.), Vol. 1-3, Cold Spring Harbor Laboratory, Cold Spring Harbor, N.Y., 2001; *Current Protocols in Molecular Biology*, Ausubel et al., eds., *Current Protocols*, a joint venture between Greene Publishing Associates, Inc. and John Wiley & Sons, Inc., (supplemented through 2006); and in Watson et al. (1992) *Recombinant DNA Second Edition*, Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, Third Edition, Wiley-Liss, New York and the references cited therein; Payne et al. (1992) *Plant Cell and Tissue Culture in Liquid Systems*, John Wiley & Sons, Inc. New York, N.Y.; Gamborg and Phillips (eds) (1995) *Plant Cell, Tissue and Organ Culture; Fundamental Methods*, Springer Lab Manual, Springer-Verlag (Berlin Heidelberg N.Y.) and Atlas and Parks (eds) *The Handbook of Microbiological Media* (1993) CRC Press, Boca Raton, Fla.

Proteins and Polypeptides of Interest

Methods of producing a protein in a cell with an unnatural amino acid at a specified position are also a feature of the invention. For example, a method includes growing, in an appropriate medium, the cell, where the cell comprises a nucleic acid that comprises at least one selector codon and encodes a protein; and, providing the unnatural amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the unnatural amino acid. A protein produced by this method is also a feature of the invention.

In certain embodiments, the O-RS comprises a bias for the aminoacylation of the cognate O-tRNA over any endogenous tRNA in an expression system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The invention also provides compositions that include proteins, where the proteins comprise an unnatural amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O-RS pairs or individual components of the invention can then be used in a host system's translation machinery, which results in an unnatural amino acid being incorporated into a protein. International Publication Numbers WO 2004/094593, filed Apr. 16, 2004, entitled "EXPANDING THE EUKARYOTIC GENETIC CODE," and WO 2002/085923, entitled "IN VIVO INCORPORATION OF UNNATURAL A NO ACIDS," describe this process, and are incorporated herein by reference. For example, when an O-tRNA/O-RS pair is introduced into a host, e.g., an *Escherichia coli* cell, the pair leads to the in vivo incorporation of an unnatural amino acid such as 7-hydroxycoumarin-ethylglycine into a protein in response to a selector codon. The unnatural amino acid that is added to the system can be a synthetic amino acid, such as a derivative of a phenylalanine or tyrosine, which can be exogenously added to the growth medium. Optionally, the compositions of the present invention can be in an in vitro translation system, or in an in vivo system(s).

A cell of the invention provides the ability to synthesize proteins that comprise unnatural amino acids in large useful quantities. In some aspects, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises an unnatural amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nL to about 100 L). The production of large quantities (e.g., greater that that typically possible with other methods, e.g., in vitro translation) of a protein in a cell including at least one unnatural amino acid is a feature of the invention.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), incorporation of labels or reactive groups, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652.

In some aspects of the invention, a composition includes at least one protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is an unnatural amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid can be found, but not limited to, those in International Publications WO 2004/094593, filed Apr. 16, 2004, entitled "EXPANDING THE EUKARYOTIC GENETIC CODE;" and, WO 2002/085923, entitled "VIVO INCORPORATION OF UNNATURAL AMINO ACIDS." Examples of therapeutic, diagnostic, and other proteins that can be modified to comprise one or more unnatural amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-19, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of unnatural amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acids) include biologically active proteins such as cytokines, inflammatory molecules, growth factors, their receptors, and oncogene products, e.g., interleukins (e.g., IL-1, IL-2, IL-8, etc.), interferons, FGF, IGF-1, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma Biosciences 2002 catalogue and price list), and the corresponding protein sequences and genes and, typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid using compositions and methods of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as Staphylococci (e.g., aureus), or Streptococci (e.g., *pneumoniae*); protozoa such as sporozoa (e.g., *Plasmodia*), *rhizopods* (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovirnses, e.g., RSV; Orthomyxovirnses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

To make a protein that includes an unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising unnatural amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology,* 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual,* Cold Spring Harbor Publications, New York, for a standard description of antibody generation, immunoassay formats and conditions that can be used to determine specific immunoreactivity. Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Use of O-tRNA and O-RS and O-tRNA/O-RS Pairs

The compositions of the invention and compositions made by the methods of the invention optionally are in a cell. The O-tRNA/O-RS pairs or individual components of the invention can then be used in a host system's translation machinery, which results in an unnatural amino acid being incorporated into a protein. International Publication Number WO 2002/085923 by Schultz, et al., entitled "IN VIVO INCORPORATION OF UNNATURAL AMINO ACIDS," describes this process and is incorporated herein by reference. For example, when an O-tRNA/O-RS pair is introduced into a host, e.g., *Escherichia coli* or yeast, the pair leads to the in vivo incorporation of an unnatural amino acid, which can be exogenously added to the growth medium, into a protein, e.g., a myoglobin test protein or a therapeutic protein, in response to a selector codon, e.g., an amber nonsense codon. Optionally, the compositions of the invention can be in an in vitro translation system, or in a cellular in vivo system(s). Proteins with the unnatural amino acid can be used in any of a wide range of applications. For example, the unnatural moiety incorporated into a protein can serve as a target for any of a wide range of modifications, for example, crosslinking with other proteins, with small molecules such as labels or dyes and/or biomolecules. With these modifications, incorporation of the unnatural amino acid can result in improved therapeutic proteins and can be used to alter or improve the catalytic function of enzymes. In some aspects, the incorporation and subsequent modification of an unnatural amino acid in a protein can facilitate studies on protein structure, interactions with other proteins, and the like.

Kits

Kits are also a feature of the invention. For example, a kit for producing a protein that comprises at least one unnatural amino acid in a cell is provided, where the kit includes at least one container containing a polynucleotide sequence encoding an O-tRNA, and/or an O-tRNA, and/or a polynucleotide sequence encoding an O-RS, and/or an O-RS. In one embodiment, the kit further includes the unnatural amino acid 7-hydroxycoumarin-ethylglycine. In another embodiment, the kit further comprises instructional materials for producing the protein and/or a host cell.

EXAMPLES

The following examples are offered to illustrate, but not to limit the claimed invention. One of skill will recognize a variety of non-critical parameters that may be altered without departing from the scope of the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

General Methodologies

All chemicals were obtained from commercial sources and used without further purification. $^1$H NMR spectra were recorded on a Bruker AMX-400 multinuclear spectrometer (Bruker BioSpin GmbH, Rheinstetten/Karlsruhe, Germany) with chemical shifts reported relative to tetramethylsilane. Protein mass spectra were acquired at the Scripps Center for Mass Spectrometry (La Jolla, Calif.).

Plasmids and Cell Lines

Plasmid pBK-lib5 encodes a library of *M. jannaschii* tyrosyl tRNA synthetase (MjTyrRS) mutants in which residues Tyr32, Leu65, Phe108, Gln109, Asp158 and Leu162 were randomized; in addition, His70 was mutated to Gly, and Ala67 was mutated to either Ala or Gly. Plasmid pREP(2)/YC encodes MjtRNA$_{CUA}^{Tyr}$, the chloramphenicol acetyltransferase (CAT) gene with a TAG codon at residue 112, the GFP gene under control of the T7 promoter, a mutant T7 RNA polymerase with a TAG codon at residues 1 and 107, and a Tet$^r$ marker. Plasmid pLWJ17B3 encodes MjtRNA$_{CUA}^{Tyr}$ under the control of the lpp promoter and rrnC terminator, the barnase gene (with three amber codons at residues 2, 44 and 65) under control of the ara promoter, and an Amp$^r$ marker. Plasmid pBAD/JYAMB-4TAG-Myo encodes the mutant sperm whale myoglobin gene with an arabinose promoter and rrnB terminator, MjtRNA$^{try}_{CUA}$ with an lpp promoter and rrnC terminator, and a tetracycline resistance marker. *E. coli* strain GeneHog®-Fis, F$^-$ mcrA Δ(mrr-hsdRMS-mcrBC) 80lacZΔM15 ΔlacX74 recA1 endA1 araD139 Δ(ara-leu) 7697 galU galK λrpsL(StrR) nupG,fis::Tn7 (DHFR) was used for studies that expressed proteins containing the unnatural amino acid L-(7-hydroxycoumarin-4-yl)ethylglycine.

Example 2

Synthesis of the Unnatural Amino Acid L-(7-Hydroxycoumarin-4-yl) Ethylglycine The unnatural coumarin amino acid L-(7-hydroxycoumarin-4-yl)ethylglycine (also written 7-hydroxycoumarin-ethylglycine; see FIG. 1, structure 1) was synthesized by first converting N-α-Cbz-L-glutamic acid α-benzyl ester into the side-chain β-keto ester, which was then reacted with resorcinol in methanesulfonic acid (von Pechmann reaction; Brun et al., *Angew. Chem., Int. Ed.*, (2004) 43:3432-3436) to afford amino acid L-(7-hydroxycoumarin-4-yl)ethylglycine. These steps are described in detail below.

Step 1—Synthesis of Ethyl Magnesium Malonate

To a stirred aqueous solution of 1.5 M magnesium chloride and 3 M ethyl potassium malonate was added five volumes of isopropanol. After filtration, ethyl magnesium malonate was dried in vacuo.

Step 2—Synthesis of (2S)-2-benzyloxycarbonylamino-5-oxo-heptanedioic acid 1-benzyl ester 7-ethyl ester (FIG. 1, structure 3)

Z-Glu-Obzl (a N-α-Cbz-L-glutamic acid α-benzyl ester) (5 g, 13.46 mmol) was dissolved in 50 ml of dry THF at room temperature. N,N'-carbonyl diimidazole (1.1 eq) was added slowly and the mixture was then stirred for 2 hrs at room temperature. Ethyl magnesium malonate (0.55 eq) was added, and the mixture was stirred at room temperature overnight. The product was extracted with ether, and washed with 10% $NaHCO_3$, water, and brine. The residue containing 3 was purified by flash chromatography on silica gel (ethyl acetate: hexanes 50:50) and concentrated on a rotary evaporator to afford a white solid in 40% yield. $^1$H-NMR (400 MHz, $CDCl_3$): δ 1.26 (t, J=7.2, 3H), 1.9-2.01 (m, 1H), 2.1-2.28 (m, 1H), 2.5-2.7 (m, 2H), 3.37 (s, 2H), 4.18 (q, J=7.2, 2H), 4.41 (s, 1H), 5.11 (s, 2H), 5.18 (s, 2H), 5.44 (d, J=8, 1H), 7.25-7.41 (m, 10H). LC-MS (ESI) calcd for $C_{24}H_2NO_7$ $(M+H^+)$ 442.18, obsd. 442.0.

Step 3: Synthesis of L-(7-hydroxycoumarin-4-yl) ethylglycine (FIG. 1. Structure 1)

(2S)-2 Benzyloxycarbonylamino-5-oxo-heptanedioic acid 1-benzyl ester 7-ethyl ester from the previous step (2.35 g, 5 mmol) was added slowly to resorcinol (3 g, 25 mmol) in methanesulfonic acid (20 ml) and stirred for two hours at room temperature. Five volumes of ether were then added to the mixture and was cooled to −30° C. The precipitate was washed with cold ether, dissolved in water, filtered, and lyophilized. L-(7-hydroxycoumarin-4-yl)ethylglycine was purified by reverse phase HPLC to afford a brown solid in 50% yield (YMC AA12S052503WT column, 12 ml/min flow rate, from 10% to 90% $CH_3CN$, 0.1% TFA (w/v) in water, over the course of 12 min). $^1$H-NMR (DMSO): δ 2.06 (s, 2H), 2.70-2.90 (m, 2H), 3.82-4.0 (m, 1H), 6.06 (s, 1H), 6.75 (dd, J=8.8, 2.4, 1H), 6.82 (d, J=2.4, 1H), 7.62 (d, J=8.8, 1H), 8.17 (s, 3H). LC-MS (ESI) calc. for $C_{13}H_{14}NO_5$ $(M+H^+)$ 264.08 Da, obsd. 264.0 Da.

Example 3

Genetic Selection of Mutant Synthetase Specific for 7-Hydroxycoumarin-Ethylglycine To selectively incorporate 7-hydroxycoumarin-ethylglycine at defined sites in proteins in *E. coli*, a mutant *Methanococcus jannaschii* tyrosyl amber suppressor tRNA (MjtRNA$^{Tyr}_{CUA}$)/tyrosyl-tRNA synthetase (MjTyrRS) pair was evolved that uniquely specifies 7-hydroxycoumarin-ethylglycine in response to the TAG selector codon.

Library Construction

To accommodate the large coumarin side chain of the unnatural amino acid 7-hydroxycoumarin-ethylglycine, an MjTyrRS library pBK-lib5 was generated, in which wild-type *Methanococcus jannaschii* tyrosyl-tRNA synthetase (FIG. 9; SEQ ID NOs: 2 and 3) His70 was mutated to Gly, and Ala67 was fixed as either Ala or Gly to increase the active site size. Six residues, Tyr-32, Leu-65, Phe-108, Gln-109, Asp-158 and Leu-162, in close proximity to bound tyrosine (Kobayashi et al., *Nat. Struct. Biol.*, (2003) 10:425-432; Zhang et al., *Protein Sci.*, (2005) 14:1340-1349) were randomized. The pBK-lib5 library consisted of 2×10$^9$ TyrRS independent clones and was constructed using standard PCR methods.

Positive/Negative Selections

Subsequently, this library was subjected to rounds of both positive and negative selections. In the positive selection, cell survival is dependent on the suppression of an amber codon introduced at a permissive site in the chloramphenicol acetyl transferase (CAT) gene when cells co-transformed with pBK-lib and MjtRNA$^{Tyr}_{CUA}$ are grown in the presence of 1 mM unnatural amino acid (UAA) and chloramphenicol (Xie and Schultz, Methods (2005) 36:227-238). Positively selected clones are then transformed into cells containing MjtRNA$^{Tyr}_{CUA}$ and a gene encoding the toxic barnase protein with three amber mutations introduced at permissive sites. These cells are grown in the absence of UAA to remove any clones that utilize endogenous amino acids (negative selection). These positive and negative selection are described in detail below.

Positive Selection—*E. coli* DH10B harboring the pREP (2)/YC plasmid was used as the host strain for the positive selection. Cells were transformed with the pBK-lib5 library, recovered in SOC for 1 hour, washed twice with glycerol minimal media with leucine (GMML) before plating on GMML-agar plates supplemented with kanamycin, chloramphenicol, tetracycline and 7-hydroxycoumarin-ethylglycine at 50 μg/mL, 60 μg/mL, 15 μg/mL and 1 mM respectively. Plates were incubated at 37° C. for 60 hours and surviving cells were scraped and plasmid DNA was extracted and purified by gel electrophoresis.

Negative Selection—The pBK-lib5 DNA was then transformed into electro-competent cells harboring the negative selection plasmid pLWJ17B3, recovered for 1 hour in SOC and then plated on LB-agar plates containing 0.2% arabinose, 50 μg/mL ampicillin and 50 μg/mL kanamycin. The plates were then incubated at 37° C. for 8-12 hours, and pBK-lib5 DNA from the surviving clones was extracted as described above.

The library was then carried through a subsequent round of positive selection, followed by a negative selection and a final round of positive selection (with chloramphenicol at 70 μg/mL). At this stage, 96 individual clones were selected and suspended in 50 μL of GMML in a 96-well plate, and replica-spotted on two sets of GMML plates. One set of GMML-agar plates was supplemented with tetracycline (15 μg/mL), kanamycin (50 μg/mL) and chloramphenicol at concentrations of 60, 80, 100 and 120 μg/mL with 1 mM 7-hydroxycoumarin-ethylglycine. The other set of plates were identical but did not contain 7-hydroxycoumarin-ethylglycine, and the chloramphenicol concentrations used were 0, 20, 40 and 60 μg/ml. After 60 hours incubation at 37° C., one clone was found to survive at 100 μg/mL chloramphenicol in the presence of 1 mM 7-hydroxycoumarin-ethylglycine, but only at 20 μg/mL chloramphenicol in the absence 7-hydroxycoumarin-ethylg-lycine. Thus, after the three rounds of positive selection and two rounds of negative selection, this library generated a single clone that grows at 100 µg/mL chloramphenicol in the presence of 7-hydroxycoumarin-ethylglycine, but only at 20 µg/mL chloramphenicol in the absence of 7-hydroxycoumarin-ethylglycine.

This clone, termed CouRS-D8, was sequenced and found to contain the following eight mutations: Tyr32Glu, Leu65His, Ala67Gly, His70Gly, Phe108Tyr, Gln109His, Asp158Gly and Leu162Gly (see FIG. 9 and SEQ D NOs: 4 and 5). The mutant synthetase polypeptide sequence provided in SEQ ID NO: 4 in FIG. 9 indicates the mutant positions in hold letters. The mutant synthetase protein is further summarized in the table below.

| Mj tyrosyl-tRNA synthetase | Amino Acid Position (codon) | | | | | | | | SEQ ID NO: |
|---|---|---|---|---|---|---|---|---|---|
| | 32 | 65 | 67 | 70 | 108 | 109 | 158 | 162 | |
| wild-type | Tyr (TAC) | Leu (TTG) | Ala (GCT) | His (CAC) | Phe (TTC) | Gln (CAG) | Asp (GAT) | Leu (TTA) | 2 (3) |
| CouRS-D8 mutant | Glu (GAG) | His (CAT) | Gly (GGT) | Gly (GGC) | Tyr (TAT) | His (CAT) | Gly (GGG) | Gly (GGT) | 4 (5) |

Four residues are mutated to glycine, most likely to create enough space to accommodate the 7-hydroxycoumarin-ethylglycine residue. Tyr32 and Asp158, which hydrogen bond to bound tyrosine in the wild-type enzyme are also mutated, consistent with the loss of activity towards tyrosine (Kobayashi et al., *Nat. Struct. Biol.*, (2003) 10:425-432; Zhang et al., *Protein Sci.*, (2005) 14:1340-1349).

Figure 8:
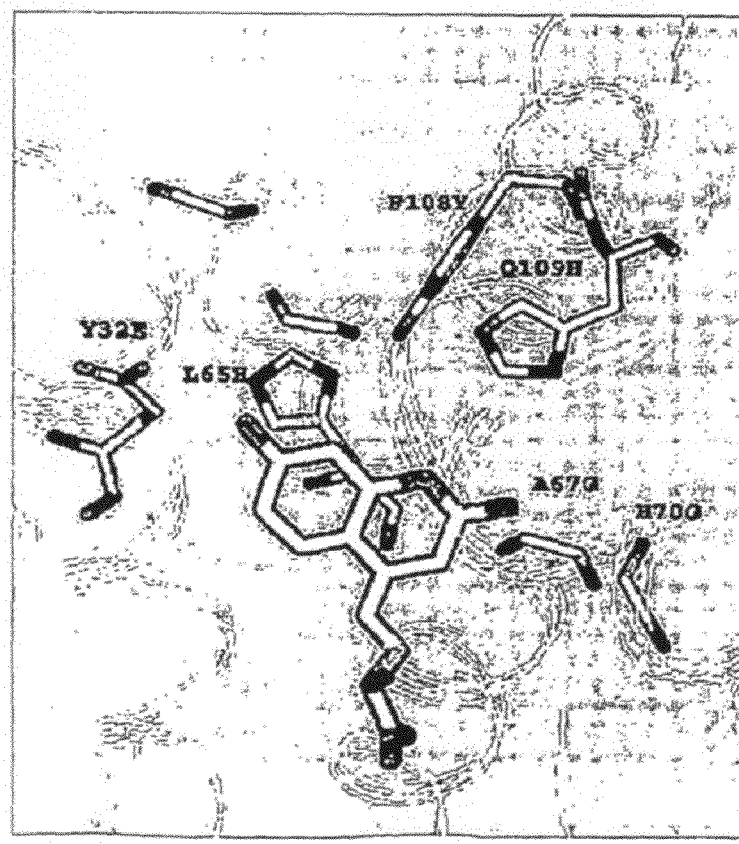
FIG. 8 provides a structural model of the mutant MjTyrRS (CouRS-D8) active site. The model was generated using the wild type MjTyrRS structure (pdb code 1J1U). The tyrosine substrate was replaced by L-(7-hydroxycoumarin-4-yl)ethylglycine, and the following mutations were indicated: Tyr32Glu, Leu65His, Ala67Gly, His70Gly, Phe108Tyr, Gln109His, Asp158Gly and Leu162Gly. The structure was optimized by energy minimization with the InsightII® software (Accelrys Software, Inc.®, San, Diego, Calif., USA).

FIG. 8 shows a predicted structural model of the mutant MjTyrRS (CouRS-D8) active site. The model was generated using the wild type MjTyrRS structure (pdb code 1J1U). The tyrosine substrate was replaced by L-(7-hydroxycoumarin-4-yl)ethylglycine, and the following mutations are shown: Tyr32Glu, Leu65His, Ala67Gly, His70Gly, Phe108Tyr, Gln1099His, Asp158Gly and Ieu162Gly. The structure was then optimized by energy minimization with the InsightII® software (Accelrys Software, Inc.®, San, Diego, Calif., USA).

Example 4

Figure 3:
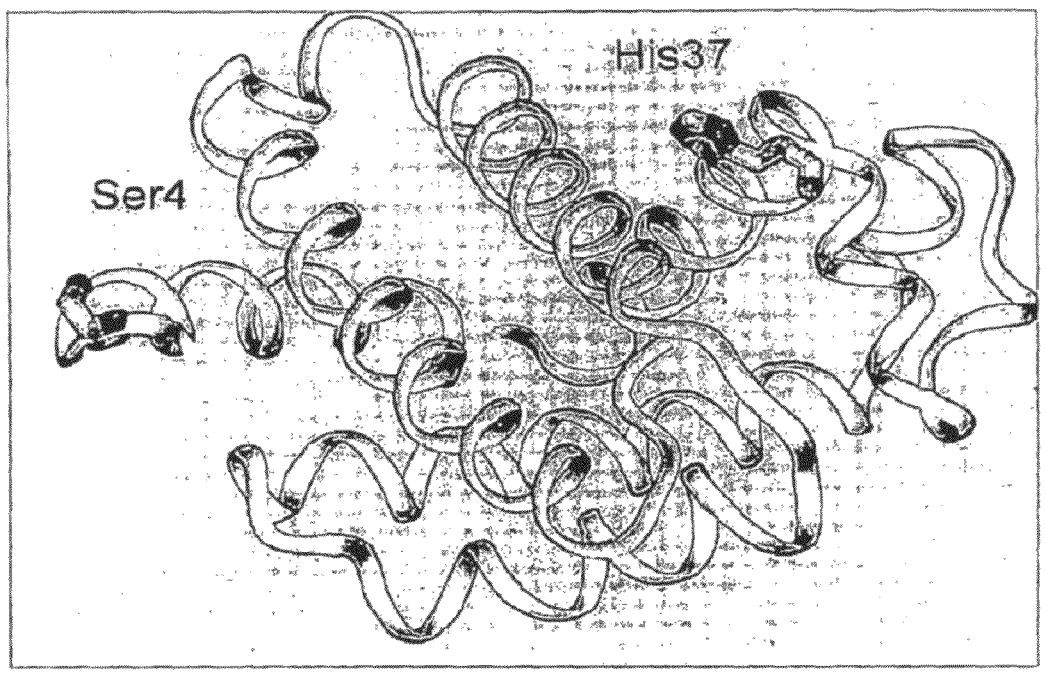
FIG. 3 provides the structure of sperm whale myoglobin (pdb code 105M). The R-groups of residues Ser4 and His37 are indicated.

Expression and Characterization of a Mutant Myoglobin Model Protein Containing 7-Hydroxycoumarin-Ethylglycine To determine the efficiency and fidelity of incorporation of 7-hydroxycoumarin-ethylglycine into proteins, an amber selector codon was substituted at either position 4 (Ser4) or position 37 (His-37) in sperm whale myoglobin (see FIG. 3) containing a C-terminal His6 tag. Protein expression was carried out in the presence of the selected synthetase CouRS-D8 and MjtRNA$^{Tyr}_{CUA}$ in *E. coli* grown in either minimal media or media supplemented with 1 mM 7-hydroxycoumarin-ethylglycine. As a negative control, protein expression was also carried out in the absence of 7-hydroxycoumarin-ethylglycine. This protein production and analysis is described in detail below.

Mutant Protein Production

Plasmids pBAD/JYAMB-4TAG-Myo or pBAD/JYAMB-37TAG-Myo were independently cotransformed with pBK vector expressing CouRS-D8 into GeneHog®-Fis *E. coli* cells. Cells were amplified in 2YT media (5 mL) supplemented with kanamycin (50 µg/mL) and tetracycline (15 µg/mL). Starter culture (1 mL) was used to inoculate 100 mL of liquid GMML or 2YT supplemented with appropriate antibiotics and 1 mM 7-hydroxycoumarin-ethylglycine. Cells were then grown at 37° C. to an OD$_{600}$ of 0.5 and protein expression was induced by the addition of 0.2% arabinose. After another 4-12 hours, cells were harvested by centrifugation. The TAG4 and TAG37 myoglobin mutants were purified by Ni-NTA affinity chromatography under native conditions. The samples were then desalted. The yield of the TAG4 and TAG37 mutant myoglobins in either media was 2 mg/L. For comparison, the yield of wild-type myoglobin under similar conditions was 5 mg/L.

Protein Mass Spectrometric Analysis

Figure 6:
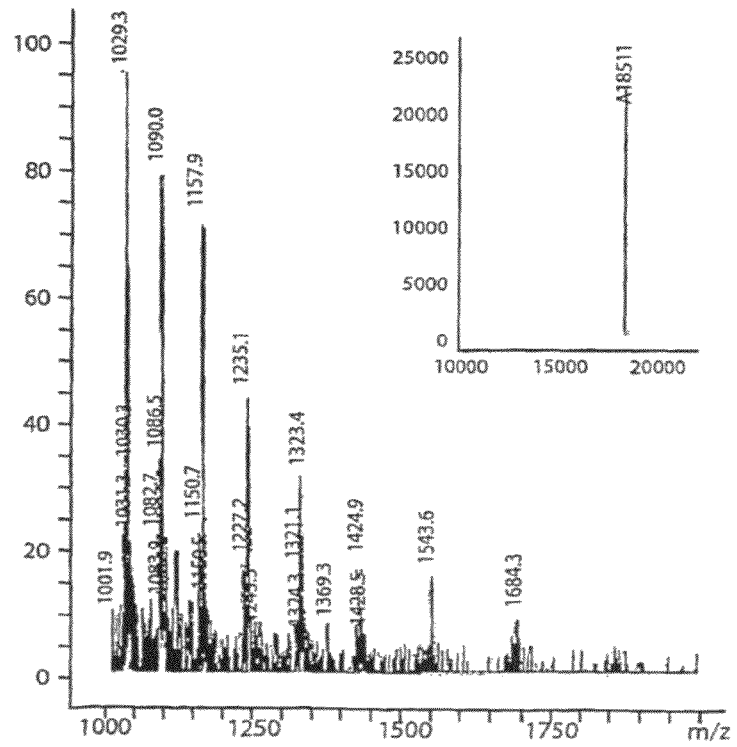
FIG. 6 provides an ESI-MS spectra of the TAG4 mutant myoglobin. The insert shows deconvoluted spectrum. Expected mass: 18512 Da; found: 18511 Da.

Purified TAG4 mutant myoglobin protein was subjected to ESI mass spectrometric analysis. ESI-mass spectrometric analyses of the mutant myoglobin gave an observed average mass M$_{avg}$ of 18511 Da, in close agreement with the calculated mass M$_{avg}$ of 18512 Da (see FIG. 6). Since species corresponding to natural amino acid incorporation was not found in the ESI-mass spectra when a convolution threshold of 5% is used, a minimum 95% incorporation purity for 7-hydroxycoumarin-ethylglycine was obtained from the signal-to-noise ratio of the protein mass spectra. The detection threshold is set such that it can only detect a species if its abundance is more than 5% of the main peak. Since only the main peak is observed, the mutant protein is >95% pure.

Protein Analysis by SDS-Page Resolution

Figure 5:
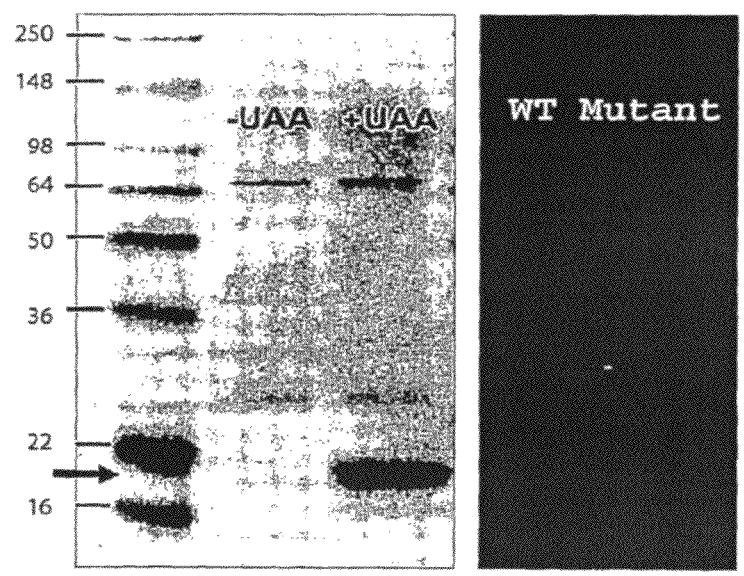
FIG. 5 provides photographs of SDS-PAGE analysis of TAG4 mutant myoglobin expression (indicated by black arrow). The center panel shows coomassie-stained SDS-PAGE resolution of proteins accumulated in the presence and absense of 1 mM L-(7-hydroxycoumarin-4-yl)ethylglycine. The right panel shows a fluorescence image of wild-type and TAG4 mutant myoglobin following resolution by SDS-PAGE. The left panel shows stained molecular mass markers.

Analysis of the purified protein by SDS-PAGE showed that full length protein was expressed only in the presence of 7-hydroxycoumarin-ethylglycine (see FIG. 5). Furthermore, the TAG4 mutant myoglobin protein incorporating the genetically encoded 7-hydroxycoumarin-ethylglycine appears as a fluorescent band after resolution on SDS-PAGE, where the wild-type myoglobin protein lacking the genetically encoded 7-hydroxycoumarin-ethylglycine did not display fluorescence. Fluorescence imaging used a STORM® fluorescence scanner (Molecular Dynamics/GE® Healthcare Life Sciences, Piscataway, N.J.).

Example 5

Use of a Genetically Encoded 7-Hydroxycoumarin-Ethylglycine as a Probe for Protein Configuration To demonstrate one of the potential uses of 7-hydroxycoumarin-ethylglycine, this amino acid was used as a probe of the urea dependent denaturation of holomyoglobin. Because coumarin fluorescence is sensitive to solvent polarity, its fluorescence intensity should correlate with local unfolding of the protein in close proximity to 7-hydroxycoumarin-ethylglycine. Myoglobin structure consist of eight helices (A to H), connected by short loops and turn (Delli Castelli et al., *Pro-* tein Sci., (2002) 11:2273-2276). Ser4 in helix A and His37 in helix C (see FIG. 3; both residues are largely solvent exposed and do not significantly interact with other nearby residues) were each independently mutated to the selector codon TAG, resulting in the in vivo genetically-programmed incorporation of 7-hydroxycoumarin-ethylglycine in the presence of the specific orthogonal O-tRNA/O-RS pair.

Figure 4:
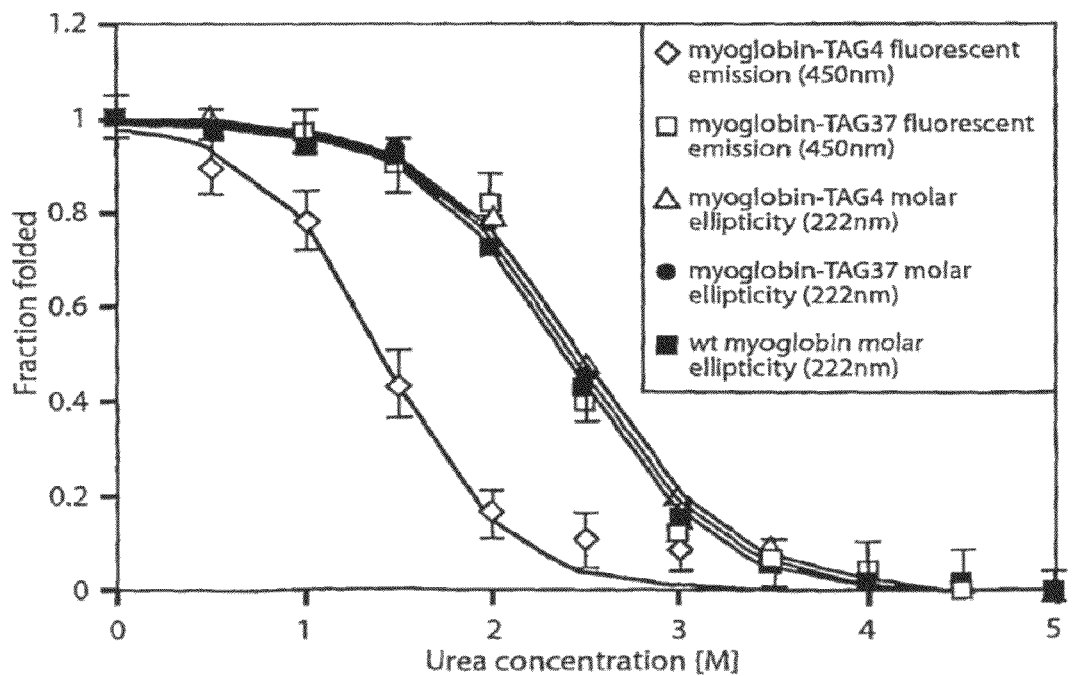
FIG. 4 provides the results of a circular dichroism analysis of urea-induced unfolding of wild-type and mutant forms of holomyoglobin. The mutant forms analyzed were either the Ser4→7-hydroxycoumarin-ethylglycine or His37→7-hydroxycoumarin-ethylglycine mutant holomyoglobins. Unfolding was monitored by both CD and the fluorescent intensity of 7-hydroxycoumarin-ethylglycine. Both experiments were carried out in 100 mM sodium phosphate buffer, pH 7.4, with various concentrations of urea as indicated. In the prescence of 5 M urea, both myoglobin mutants show a 30% increase in fluorescence signal compared to 0 M urea. The "fraction folded" is calculated by normalizing the fluorescence signal or molar ellipticity at 5 M urea to the fully unfolded state.

As indicated in FIG. 4, the urea induced unfolding curves of the wild type, Ser4→7-hydroxycoumarin-ethylglycine and His37→7-hydroxycoumarin-ethylglycine holomyoglobins as monitored by circular dichroism are virtually identical, suggesting that introduction of 7-hydroxycoumarin-ethylglycine into either helix A or helix C does not significantly perturb protein stability. At 2 M urea concentration, the fluorescence intensity of 7-hydroxycoumarin-ethylglycine at position 4 in holomyogloin increases 30% (and remains at this level from 2 M to 5 M urea), suggesting that this region of the protein is disordered (Zhang et al., Protein Sci., (2005) 14:1340-1349). In contrast, mutant myoglobin with 7-hydroxycoumarin-ethylglycine at residue 37 shows little change in its fluorescence intensity at 2 M urea, but undergoes a similar fluorescence increase at 3 M urea. Consistent with this result, a previous NMR study has shown that when the urea concentration is higher than 2.2 M, helix A and B are largely disordered, as shown by the disappearance of short and medium range NOEs in this region, whereas helices C, D, and F unfold later, when the urea concentration is higher than 3.0 M (Delli Castelli et al., Protein Sci., (2002) 11:2273-2276). Thus it appears that amino acid 7-hydroxycoumarin-ethylglycine is a site-specific probe of protein conformational changes, in contrast to circular dichroism which reports global changes averaged over the entire structure.

Figure 7:
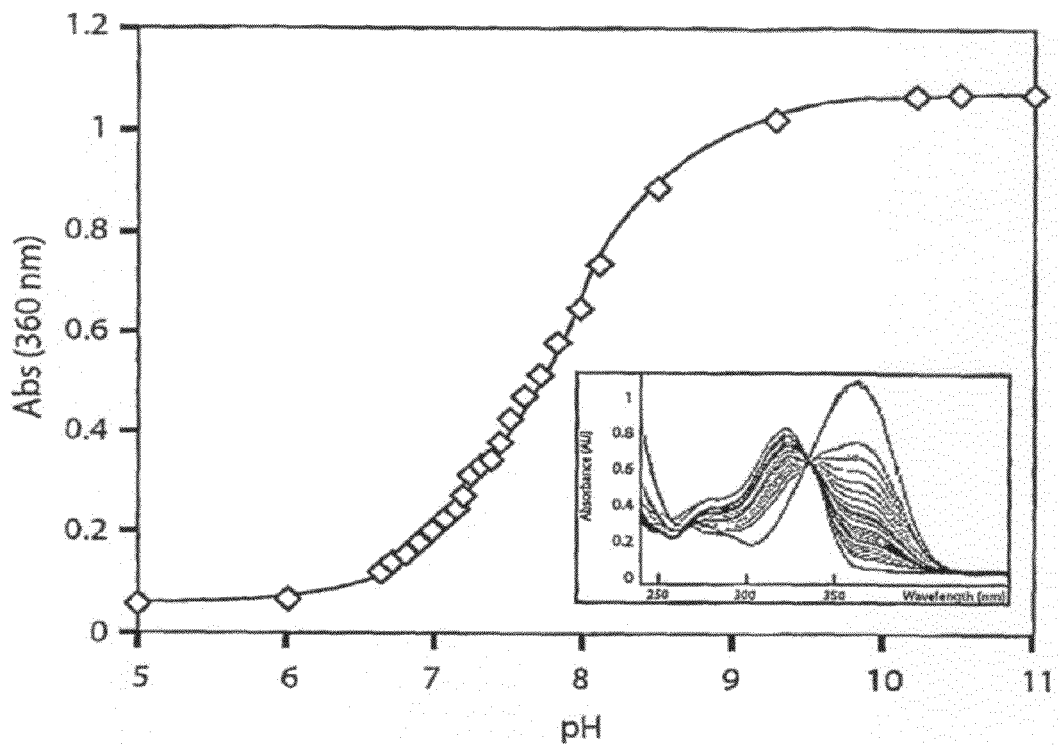
FIG. 7 provides an absorption spectrum of 60 μM coumarinyl amino acid L-(7-hydroxycoumarin-4-yl)ethylglycine in 100 mM sodium phosphate buffer.

The sensitivity of 7-hydroxycoumarin-ethylglycine to pH was also tested, as shown in FIG. 7. The absorption spectrum of 60 µM coumarinyl amino acid 7-hydroxycoumarin-ethylglycine was measured in 100 mM sodium phosphate buffer. The absorbance of 360 nM increased while pH increased. A pKa of 7.8 was calculated from these measurements.

The sensitivity of 7-hydroxycoumarin-ethylglycine to pH (see FIG. 7) and solvent polarity (Zinsli, J. Photochem (1974) 3:55-69) should make it a useful probe for many biological studies, both in vitro and in vivo (Brun et al., Angew. Chem., Int. Ed, (2004) 43:3432-3436). For example, amino acid 7-hydroxycoumarin-ethylglycine can be used to monitor bimolecular interactions or conformational changes in proteins, or the topology of membrane bound proteins. In addition, because 7-hydroxycoumarin-ethylglycine has a pKa of 7.8, which can be systematically altered by substitution of the coumarin ring (Sun et al., Bioorg. Med. Chem. Lett., (1998) 8:3107-3110), it should be a useful probe of organellar pH, and pH dependent cellular processes. Moreover, in its excited state, 7-hydroxycoumarin is both a strong photo-acid (Cohen and Huppert, Phys. Chem. A (2001) 105:7157-7164) and may facilitate the study of proton transfer processes in proteins.

While the foregoing invention has been described in some detail for purposes of clarity and understanding, it will be clear to one skilled in the art from a reading of this disclosure that various changes in form and detail can be made without departing from the true scope of the invention. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A translation system comprising:
    (a) a first unnatural amino acid that is an L-(7-hydroxycoumarin-4-yl)ethylglycine unnatural amino acid;
    (b) a first orthogonal aminoacyl-tRNA synthetase (O-RS), wherein said first O-RS comprises the amino acid sequence set forth in SEQ ID NO: 4, or a conservative variant thereof, which conservative variant is at least 90% identical to SEQ ID NO: 4 and comprises a Glu at amino acid position 32; a Gly or Ala at amino acid position 67; a Gly at amino acid position 70; and a Gly at amino acid position 158; and,
    (c) a first orthogonal tRNA (O-tRNA);
wherein said first O-RS preferentially aminoacylates said first O-tRNA with said first unnatural amino acid.

2. The translation system of claim 1, wherein said first O-RS is derived from a *Methanococcus jannaschii* aminoacyl-tRNA synthetase.

3. The translation system of claim 1, wherein said first O-RS is derived from a wild-type *Methanococcus jannaschii* tyrosyl-tRNA synthetase.

4. The translation system of claim 1, wherein said first O-tRNA is an amber suppressor tRNA.

5. The translation system of claim 1, wherein said first O-tRNA comprises or is encoded by the polynucleotide sequence set forth in SEQ ID NO: 1.

6. The translation system of claim 1, further comprising a nucleic acid encoding a protein of interest, said nucleic acid comprising at least one selector codon, wherein said selector codon is recognized by said first O-tRNA.

7. The translation system of claim 6, further comprising a second O-RS and a second O-tRNA, wherein the second O-RS preferentially aminoacylates the second O-tRNA with a second unnatural amino acid that is different from the first unnatural amino acid, and wherein the second O-tRNA recognizes a selector codon that is different from the selector codon recognized by the first O-tRNA.

8. The translation system of claim 1, wherein said system comprises a host cell comprising said first unnatural amino acid, said first O-RS and said first O-tRNA.

9. The translation system of claim 8, wherein said host cell is a eubacterial cell.

10. The translation system of claim 9, wherein said eubacterial cell is an *E. coli* cell.

11. The translation system of claim 8, wherein said host cell comprises a polynucleotide encoding said first O-RS.

12. The translation system of claim 11, wherein said polynucleotide comprises the nucleotide sequence set forth in SEQ ID NO: 5.

13. The translation system of claim 8, wherein said host cell comprises a polynucleotide encoding said first O-tRNA.

14. A method for producing in a translation system a protein comprising an unnatural amino acid at a selected position, the method comprising:
    (a) providing a translation system comprising:
        (i) a first unnatural amino acid that is an L-(7-hydroxycoumarin-4-yl)ethylglycine unnatural amino acid;
        (ii) a first orthogonal aminoacyl-tRNA synthetase (O-RS), wherein said first O-RS comprises the amino acid sequence set forth in SEQ ID NO: 4, or a conservative variant thereof, which conservative variant is at least 90% identical to SEQ ID NO: 4 and comprises a Glu at amino acid position 32; a Gly or Ala at amino acid position 67; a Gly at amino acid position 70; and a Gly at amino acid position 158;

(iii) a first orthogonal tRNA (O-tRNA), wherein said first O-RS preferentially aminoacylates said first O-tRNA with said unnatural amino acid; and, (iv) a nucleic acid encoding said protein, wherein said nucleic acid comprises at least one selector codon that is recognized by said first O-tRNA; and, (b) incorporating said unnatural amino acid at said selected position in said protein during translation of said protein in response to said selector codon, thereby producing said protein comprising said unnatural amino acid at the selected position.

15. The method of claim 14, wherein said providing a translation system comprises providing the polynucleotide encoding said O-RS.

16. The method of claim 14, wherein said providing a translation system comprises providing an O-RS derived from a *Methanococcus jannaschii* aminoacyl-tRNA synthetase.

17. The method of claim 14, wherein said providing a translation system comprises providing an O-RS derived from a wild-type *Methanococcus jannaschii* tyrosyl-tRNA synthetase.

18. The method of claim 14, wherein said providing a translation system comprises mutating an amino acid binding pocket of a wild-type aminoacyl-tRNA synthetase by site-directed mutagenesis, and selecting a resulting O-RS that preferentially aminoacylates said O-tRNA with said unnatural amino acid.

19. The method of claim 18, wherein said selecting step comprises positively selecting and negatively selecting for said O-RS from a pool comprising a plurality of resulting aminoacyl-tRNA synthetase molecules following site-directed mutagenesis.

20. The method of claim 14, wherein said providing a translation system comprises providing a polynucleotide encoding said O-tRNA.

21. The method of claim 14, wherein said providing a translation system comprises providing an O-tRNA that is an amber suppressor tRNA.

22. The method of claim 14, wherein said providing a translation system comprises providing an O-tRNA that comprises or is encoded by the polynucleotide sequence set forth in SEQ ID NO: 1.

23. The method of claim 14, wherein said providing a translation system comprises providing a nucleic acid comprising an amber selector codon.

24. The method of claim 14, wherein said protein further comprises a second unnatural amino acid that is different from said first unnatural amino acid, and wherein said translation system further comprises a second O-RS and a second O-tRNA, wherein the second O-RS preferentially aminoacylates the second O-tRNA with a second unnatural amino acid that is different from the first unnatural amino acid, and wherein the second O-tRNA recognizes a selector codon in the nucleic acid that is different from the selector codon recognized by the first O-tRNA.

25. The method of claim 14, wherein said providing a translation system comprises providing a host cell, wherein said host cell comprises said first unnatural amino acid, said first O-RS, said first O-tRNA and said nucleic acid, and wherein said incorporating step comprises culturing said host cell.

26. The method of claim 25, wherein said providing a host cell comprises providing a eubacterial host cell.

27. The method of claim 26, wherein said providing a eubacterial host cell comprises providing an *E. coli* host cell.

28. The method of claim 25, wherein said providing a host cell comprises providing a host cell comprising a polynucleotide encoding said O-RS.

29. The method of claim 28, wherein said providing a host cell comprising a polynucleotide encoding said O-RS step comprises providing a host cell comprising a polynucleotide comprising the nucleotide sequence set forth in SEQ ID NO: 5.

30. The method of claim 14, wherein said providing a translation system comprises providing a cell extract.

31. A composition comprising the polypeptide set forth in SEQ ID NO: 4, or a conservative variant thereof, which conservative variant is at least 90% identical to SEQ ID NO: 4 and comprises a Glu at amino acid position 32; a Gly or Ala at amino acid position 67; a Gly at amino acid position 70; and a Gly at amino acid position 158, wherein the conservative variant polypeptide aminoacylates a cognate orthogonal tRNA (O-tRNA) with an L-(7-hydroxycoumarin-4-yl)ethylglycine unnatural amino acid.

32. A polynucleotide encoding the polypeptide of claim 31.

33. The polynucleotide of claim 32, wherein said polynucleotide comprises the nucleotide sequence of SEQ ID NO: 5.

34. The composition of claim 31, where said composition is a cell comprising the polypeptide.

35. A composition comprising the polynucleotide comprising a nucleotide sequence set forth in SEQ ID NO: 5.

36. A vector comprising the polynucleotide of claim 35.

37. An expression vector comprising the polynucleotide of claim 35.

38. A cell comprising a vector, the vector comprising the polynucleotide of claim 35.

* * * * *